(12) United States Patent
Wilson et al.

(10) Patent No.: US 8,163,008 B2
(45) Date of Patent: Apr. 24, 2012

(54) LEAFLET VALVE

(75) Inventors: Robert Foster Wilson, Roseville, MN (US); Scott Robert Wilson, Maple Grove, MN (US); James L. Pokorney, Northfield, MN (US)

(73) Assignee: Heart Leaflet Technologies, Inc., Maple Grove, MN (US)

( * ) Notice: Subject to any disclaimer, the term of this patent is extended or adjusted under 35 U.S.C. 154(b) by 958 days.

(21) Appl. No.: 12/037,025

(22) Filed: Feb. 25, 2008

(65) Prior Publication Data
US 2008/0147105 A1   Jun. 19, 2008

Related U.S. Application Data

(63) Continuation of application No. 10/651,162, filed on Aug. 28, 2003, now Pat. No. 7,335,218.

(60) Provisional application No. 60/407,414, filed on Aug. 28, 2002.

(51) Int. Cl.
A61F 2/24   (2006.01)
(52) U.S. Cl. ....................... 623/2.11; 606/167
(58) Field of Classification Search .............. 606/184, 606/185, 170, 174, 180, 167; 600/562, 16–18, 600/37; 623/2.11, 904
See application file for complete search history.

(56) References Cited

U.S. PATENT DOCUMENTS

| | | |
|---|---|---|
| 15,192 A | 6/1856 | Peale |
| 3,464,065 A | 9/1969 | Cromie |
| 3,739,402 A | 6/1973 | Cooley et al. |
| 3,800,403 A | 4/1974 | Anderson et al. |
| 3,996,938 A | 12/1976 | Clark, III |
| 3,997,923 A | 12/1976 | Possis |
| 4,056,854 A | 11/1977 | Boretos et al. |
| 4,084,268 A | 4/1978 | Ionescu et al. |
| 4,470,157 A | 9/1984 | Love |
| 4,650,466 A | 3/1987 | Luther |
| 4,680,031 A | 7/1987 | Alonso |
| 4,921,484 A | 5/1990 | Hillstead |
| 4,994,077 A | 2/1991 | Dobben |
| 5,032,128 A | 7/1991 | Alonso |
| 5,041,093 A | 8/1991 | Chu |
| 5,046,497 A | 9/1991 | Millar |
| 5,071,407 A | 12/1991 | Termin et al. |
| 5,180,368 A | 1/1993 | Garrison |

(Continued)

FOREIGN PATENT DOCUMENTS
DE   102005052628 A1   5/2007
(Continued)

OTHER PUBLICATIONS

Japanese Patent Office, Examiner's Report mailed Sep. 28, 2011 in Japanese Patent Application No. JP2008-513838, 7 pages.

(Continued)

*Primary Examiner* — Kevin T Truong
(74) *Attorney, Agent, or Firm* — Inskeep IP Group, Inc.

(57) ABSTRACT

A device and method for improving flow through a native blood vessel valve, such as the aortic valve, are provided. The present invention allows a miniature valve to be implanted into affected leaflets percutaneously, obviating the need for coronary bypass surgery. The method includes the cutting of small holes, on the order of 4 mm, in the leaflets of a targeted valve, thereby allowing blood to flow through the newly formed holes. The holes are used as attachment sites for the miniature valves of the present invention.

18 Claims, 20 Drawing Sheets

U.S. PATENT DOCUMENTS

| | | |
|---|---|---|
| 5,221,261 A | 6/1993 | Termin et al. |
| 5,222,971 A | 6/1993 | Willard et al. |
| 5,258,023 A | 11/1993 | Reger |
| 5,326,372 A | 7/1994 | Mhatre et al. |
| 5,332,402 A | 7/1994 | Teitelbaum |
| 5,336,258 A | 8/1994 | Quintero et al. |
| 5,397,351 A | 3/1995 | Pavcnik et al. |
| 5,409,019 A | 4/1995 | Wilk |
| 5,411,552 A | 5/1995 | Andersen et al. |
| 5,429,144 A | 7/1995 | Wilk |
| 5,456,667 A | 10/1995 | Ham et al. |
| 5,487,760 A | 1/1996 | Villafana |
| 5,496,277 A | 3/1996 | Termin et al. |
| 5,496,329 A | 3/1996 | Reisinger |
| 5,500,014 A | 3/1996 | Quijano et al. |
| 5,514,181 A | 5/1996 | Light et al. |
| 5,571,175 A | 11/1996 | Vanney |
| 5,599,329 A | 2/1997 | Gabbay |
| 5,607,466 A | 3/1997 | Imbert et al. |
| 5,720,764 A | 2/1998 | Naderlinger |
| 5,725,552 A | 3/1998 | Kotula et al. |
| 5,725,571 A | 3/1998 | Imbert et al. |
| 5,749,883 A | 5/1998 | Halpern |
| 5,827,316 A | 10/1998 | Young et al. |
| 5,840,081 A | 11/1998 | Andersen et al. |
| 5,846,261 A | 12/1998 | Kotula et al. |
| 5,855,601 A | 1/1999 | Bessler et al. |
| 5,855,614 A | 1/1999 | Stevens et al. |
| 5,868,708 A | 2/1999 | Hart et al. |
| 5,898,263 A | 4/1999 | Itou et al. |
| 5,924,424 A | 7/1999 | Stevens et al. |
| 5,925,060 A | 7/1999 | Forber |
| 5,928,260 A | 7/1999 | Chin et al. |
| 5,935,139 A | 8/1999 | Bates |
| 5,944,738 A | 8/1999 | Amplatz et al. |
| 5,957,949 A | 9/1999 | Leonhardt et al. |
| 5,961,549 A | 10/1999 | Nguyen et al. |
| 5,972,017 A | 10/1999 | Berg et al. |
| 5,980,455 A | 11/1999 | Daniel et al. |
| 5,989,263 A | 11/1999 | Shmulewitz |
| 6,010,531 A | 1/2000 | Donlon et al. |
| 6,015,431 A | 1/2000 | Thornton et al. |
| 6,016,810 A | 1/2000 | Ravenscroft |
| 6,036,702 A | 3/2000 | Bachinski et al. |
| 6,074,416 A | 6/2000 | Berg et al. |
| 6,074,418 A | 6/2000 | Buchanan et al. |
| 6,096,053 A | 8/2000 | Bates |
| 6,106,497 A | 8/2000 | Wang |
| 6,113,612 A | 9/2000 | Swanson et al. |
| 6,120,432 A | 9/2000 | Sullivan et al. |
| 6,123,715 A | 9/2000 | Amplatz |
| 6,126,686 A | 10/2000 | Badylak et al. |
| 6,146,396 A | 11/2000 | Kónya et al. |
| 6,149,681 A | 11/2000 | Houser et al. |
| 6,165,183 A | 12/2000 | Kuehn et al. |
| 6,165,215 A | 12/2000 | Rottenberg et al. |
| 6,168,614 B1 | 1/2001 | Andersen et al. |
| 6,168,616 B1 | 1/2001 | Brown, III |
| 6,171,335 B1 | 1/2001 | Wheatley et al. |
| 6,197,043 B1 | 3/2001 | Davidson |
| 6,200,336 B1 | 3/2001 | Pavcnik et al. |
| 6,287,334 B1 | 9/2001 | Moll et al. |
| 6,293,955 B1 | 9/2001 | Houser et al. |
| 6,312,465 B1 | 11/2001 | Griffin et al. |
| 6,325,816 B1 | 12/2001 | Fulton, III et al. |
| 6,334,873 B1 | 1/2002 | Lane et al. |
| 6,336,937 B1 | 1/2002 | Vonesh et al. |
| 6,338,740 B1 | 1/2002 | Carpentier |
| 6,344,048 B1 | 2/2002 | Chin et al. |
| 6,358,277 B1 | 3/2002 | Duran |
| 6,358,279 B1 | 3/2002 | Tahi et al. |
| 6,378,028 B2 | 4/2002 | Inagawa et al. |
| 6,383,205 B1 | 5/2002 | Samson et al. |
| 6,402,780 B2 | 6/2002 | Williamson, IV et al. |
| 6,419,681 B1 | 7/2002 | Vargas et al. |
| 6,423,090 B1 | 7/2002 | Hancock |
| 6,425,916 B1 | 7/2002 | Garrison et al. |
| 6,440,163 B1 | 8/2002 | Swanson et al. |
| 6,440,164 B1 | 8/2002 | DiMatteo et al. |
| 6,454,798 B1 | 9/2002 | Moe |
| 6,454,799 B1 | 9/2002 | Schreck |
| 6,458,153 B1 | 10/2002 | Bailey et al. |
| 6,475,239 B1 | 11/2002 | Campbell et al. |
| 6,478,028 B1 | 11/2002 | Paolitto et al. |
| 6,494,889 B1 | 12/2002 | Fleischman et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,511,491 B2 | 1/2003 | Grudem et al. |
| 6,524,339 B1 | 2/2003 | Adams |
| 6,582,451 B1 | 6/2003 | Marucci et al. |
| 6,592,614 B2 | 7/2003 | Lenker et al. |
| 6,613,078 B1 | 9/2003 | Barone |
| 6,616,675 B1 | 9/2003 | Evard et al. |
| 6,626,930 B1 | 9/2003 | Allen et al. |
| 6,635,068 B1 | 10/2003 | Dubrul et al. |
| 6,652,578 B2 | 11/2003 | Bailey et al. |
| 6,673,042 B1 | 1/2004 | Samson et al. |
| 6,673,088 B1 | 1/2004 | Vargas et al. |
| 6,719,781 B1 | 4/2004 | Kim |
| 6,758,855 B2 | 7/2004 | Fulton, III et al. |
| 6,769,434 B2 | 8/2004 | Liddicoat et al. |
| 6,893,457 B2 | 5/2005 | Dong |
| 6,929,653 B2 | 8/2005 | Strecter |
| 6,994,689 B1 | 2/2006 | Zadno-Azizi et al. |
| 7,156,861 B2 | 1/2007 | Scribner et al. |
| 7,217,287 B2 * | 5/2007 | Wilson et al. ............... 623/2.11 |
| 7,232,432 B2 | 6/2007 | Fulton, III et al. |
| 7,255,695 B2 | 8/2007 | Falwell et al. |
| 7,306,594 B2 | 12/2007 | Collins et al. |
| 7,329,279 B2 | 2/2008 | Haug et al. |
| RE40,377 E | 6/2008 | Williamson |
| 7,399,315 B2 | 7/2008 | Iobbi |
| 7,445,630 B2 | 11/2008 | Lashinski et al. |
| 7,479,152 B2 | 1/2009 | Fulton, III et al. |
| 7,524,319 B2 | 4/2009 | Dubrul |
| 7,621,866 B2 * | 11/2009 | Dietz et al. ...................... 600/37 |
| 7,841,976 B2 * | 11/2010 | McBride et al. ................ 600/16 |
| 2001/0007956 A1 | 7/2001 | Letac et al. |
| 2001/0010017 A1 | 7/2001 | Letac et al. |
| 2001/0012949 A1 | 8/2001 | Forber |
| 2001/0021872 A1 | 9/2001 | Bailey et al. |
| 2001/0039450 A1 | 11/2001 | Pavcnik et al. |
| 2001/0049555 A1 | 12/2001 | Gabbay |
| 2002/0013571 A1 | 1/2002 | Goldfarb et al. |
| 2002/0026238 A1 | 2/2002 | Lane et al. |
| 2002/0032481 A1 | 3/2002 | Gabbay |
| 2002/0055772 A1 | 5/2002 | McGuckin, Jr. et al. |
| 2002/0107565 A1 | 8/2002 | Greenhalgh |
| 2002/0111620 A1 | 8/2002 | Cooper et al. |
| 2002/0123802 A1 | 9/2002 | Snyders |
| 2002/0178842 A1 | 12/2002 | Taylor |
| 2002/0188344 A1 | 12/2002 | Bolea et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2004/0073293 A1 | 4/2004 | Thompson |
| 2004/0073301 A1 | 4/2004 | Donlon et al. |
| 2004/0092858 A1 | 5/2004 | Wilson et al. |
| 2004/0171978 A1 | 9/2004 | Shalaby |
| 2004/0220664 A1 | 11/2004 | Chobotov |
| 2004/0260333 A1 | 12/2004 | Dubrul et al. |
| 2005/0137691 A1 | 6/2005 | Salahieh et al. |
| 2005/0137694 A1 | 6/2005 | Haug et al. |
| 2005/0137702 A1 | 6/2005 | Haug et al. |
| 2005/0177182 A1 | 8/2005 | Van Der Burg et al. |
| 2005/0240200 A1 | 10/2005 | Bergheim |
| 2005/0251251 A1 | 11/2005 | Cribier |
| 2005/0283231 A1 | 12/2005 | Haug et al. |
| 2006/0074484 A1 | 4/2006 | Huber |
| 2006/0129235 A1 | 6/2006 | Seguin et al. |
| 2006/0142848 A1 | 6/2006 | Gabbay |
| 2006/0167468 A1 | 7/2006 | Gabbay |
| 2006/0173533 A1 | 8/2006 | Chobotov |
| 2006/0271166 A1 | 11/2006 | Thill et al. |
| 2007/0010876 A1 | 1/2007 | Salahieh et al. |

| 2007/0203517 | A1 | 8/2007 | Williams et al. |
| 2009/0076598 | A1 | 3/2009 | Salahieh et al. |
| 2009/0222076 | A1 | 9/2009 | Figulla et al. |

FOREIGN PATENT DOCUMENTS

| EP | 0533511 A1 | 3/1993 |
| EP | 0850607 A1 | 7/1998 |
| FR | 0014992 A1 | 11/2000 |
| FR | 2 816 826 A1 | 5/2002 |
| JP | 2002-537943 A | 11/2002 |
| JP | 2003-506133 A | 2/2003 |
| JP | 2003-518984 A | 6/2003 |
| JP | 2004-503327 A | 2/2004 |
| WO | WO 97/27799 A1 | 8/1997 |
| WO | WO 97/30659 A1 | 8/1997 |
| WO | WO 99/15112 A1 | 4/1999 |
| WO | WO 99/40868 A1 | 8/1999 |
| WO | WO 00/15149 A1 | 3/2000 |
| WO | WO 00/44311 A2 | 8/2000 |
| WO | WO 00/47139 A1 | 8/2000 |
| WO | WO 01/28432 A1 | 4/2001 |
| WO | WO 02/04037 A1 | 1/2002 |
| WO | WO 02/24119 A1 | 3/2002 |
| WO | WO 02/36048 A1 | 5/2002 |
| WO | WO 03/011195 A2 | 2/2003 |
| WO | WO 2007/041782 A1 | 4/2007 |
| WO | WO 2009/124288 A1 | 10/2009 |

OTHER PUBLICATIONS

IP Australia, Notice of Acceptance mailed Sep. 15, 2011 in Australian Patent Application No. AU2006251938, 3 pages.
WIPO, U.S. International Search Authority, International Search Report and Written Opinion mailed Aug. 17, 2011 in International Patent Application No. PCT/US2011/035983, 7 pages.
State Intellectual Property Office, P.R. China, Office Action mailed Jul. 29, 2011 in Chinese Patent Application No. CN201010533068.8, 4 pages.
United States Patent and Trademark Office, Final Office Action mailed Jul. 8, 2011 in U.S. Appl. No. 11/864,557, 8 pages.
IP Australia, Office Action mailed Apr. 18, 2011 in Australian Patent Application No. AU2006251938, 2 pages.
Japanese Patent Office, Examiner's Report mailed Feb. 16, 2011 in Japanese Patent Application No. 2008-513825, 5 pages.
IP Australia, Office Action mailed Jan. 25, 2011 in Australian Patent Application No. AU2006251990, 3 pages.
Israel Patent Office, Office Action mailed Jan. 25, 2011 in Israeli Patent Application No. IL197867, 3 pages.
Canadian Intellectual Property Office, Notice of Allowance mailed Jan. 18, 2011 in Canadian Patent Application No. 2,503,258, 1 page.
United States Patent and Trademark Office, Office Action mailed Dec. 29, 2010 in U.S. Appl. No. 11/864,557, 13 pages.
United States Patent and Trademark Office, Final Office Action mailed Dec. 14, 2010 in U.S. Appl. No. 11/443,814, 10 pages.
United States Patent and Trademark Office, Final Office Action mailed Dec. 14, 2010 in U.S. Appl. No. 11/443,814, 10 pages.
European Patent Office, Supplementary European Search Report dated Nov. 3, 2010 in European Patent Application No. EP03749171.9-1257, 6 pages.
State Intellectual Property Office, P.R. China, Notification to Grant Patent Right for Invention mailed Aug. 3, 2010 in Chinese Patent Application No. 200680027512.0, 5 pages.
United States Patent and Trademark Office, Final Office Action mailed Jul. 27, 2010 in U.S. Appl. No. 12/037,025, 10 pages.
United States Patent and Trademark Office, Final Office Action mailed Jul. 22, 2010 in U.S. Appl. No. 11/443,814, 9 pages.
United States Patent and Trademark Office, Final Office Action mailed Jul. 22, 2011 in U.S. Appl. No. 11/443,814, 9 pages.
United States Patent and Trademark Office, Final Office Action mailed Mar. 17, 2010 in U.S. Appl. No. 11/442,371, 8 pages.
Canadian Intellectual Property Office, Office Action mailed Mar. 9, 2010 in Canadian Patent Application No. 2,503,258, 2 pages.
United States Patent and Trademark Office, Office Action mailed Jan. 22, 2010 in U.S. Appl. No. 12/037,025, 11 pages.
United States Patent and Trademark Office, Office Action mailed Dec. 29, 2009 in U.S. Appl. No. 11/443,814, 7 pages.
United States Patent and Trademark Office, Office Action mailed Dec. 20, 2009 in U.S. Appl. No. 11/443,814, 7 pages.
State Intellectual Property Office, P.R. China, Office Action mailed Dec. 11, 2009 in Chinese Patent Application No. CN200680027665.5, 6 pages.
IP Australia, Office Action mailed Dec. 2, 2009 in Australian Patent Application No. AU2003268220, 3 pages.
State Intellectual Property Office, P.R. China, Examiner's Report mailed Nov. 27, 2009 in Chinese Patent Application No. CN200680027512.0, 6 pages.
State Intellectual Property Office, P.R. China, Office Action mailed Nov. 27, 2009 in Chinese Patent Application No. CN200680027512.0, 6 pages.
United States Patent and Trademark Office, Office Action mailed Sep. 3, 2009 in U.S. Appl. No. 11/442,371, 7 pages.
IP Australia, Office Action mailed Jul. 7, 2009 in Australian Patent Application No. AU2003268220, 6 pages.
United States Patent and Trademark Office, Final Office Action mailed May 4, 2009 in U.S. Appl. No. 12/037,025, 9 pages.
United States Patent and Trademark Office, Final Office Action mailed Apr. 23, 2009 in U.S. Appl. No. 11/442,371, 6 pages.
United States Patent and Trademark Office, Office Action mailed Apr. 17, 2009 in U.S. Appl. No. 11/443,814, 7 pages.
United States Patent and Trademark Office, Office Action mailed Apr. 17, 2009 in U.S. Appl. No. 11/443,814, 7 pages.
United States Patent and Trademark Office, Final Office Action mailed Nov. 17, 2008 in U.S. Appl. No. 11/443,814, 10 pages.
United States Patent and Trademark Office, Final Office Action mailed Nov. 17, 2008 in U.S. Appl. No. 11/443,814, 10 pages.
United States Patent and Trademark Office, Office Action mailed Nov. 7, 2008 in U.S. Appl. No. 12/037,025, 11 pages.
United States Patent and Trademark Office, Office Action mailed Oct. 20, 2008 in U.S. Appl. No. 11/442,371, 10 pages.
United States Patent and Trademark Office, Final Office Action mailed Jun. 17, 2008 in U.S. Appl. No. 12/037,025, 11 pages.
IP Australia, Office Action mailed Apr. 3, 2008 in Australian Patent Application No. AU2003268220, 3 pages.
United States Patent and Trademark Office, Office Action mailed Mar. 18, 2008 in U.S. Appl. No. 11/443,814, 10 pages.
United States Patent and Trademark Office, Office Action mailed Mar. 18, 2008 in U.S. Appl. No. 11/443,814, 10 pages.
WIPO, U.S. International Search Authority, International Search Report and Written Opinion mailed Mar. 13, 2008 in International Patent Application No. PCT/US2007/079978, 9 pages.
WIPO, U.S. International Preliminary Examining Authority, International Preliminary Report on Patentability mailed Dec. 13, 2007 in International Patent Application No. PCT/US2006/021021, 7 pages.
WIPO, U.S. International Preliminary Examining Authority, International Preliminary Report on Patentability mailed Nov. 30, 2007 in International Patent Application No. PCT/US2006/020975, 4 pages.
United States Patent and Trademark Office, Notice of Allowance mailed Sep. 25, 2007 in U.S. Appl. No. 10/651,162, 4 pages.
United States Patent and Trademark Office, Office Action mailed Sep. 10, 2007 in U.S. Appl. No. 12/037,025, 12 pages.
WIPO, U.S. International Search Authority, International Search Report and Written Opinion mailed Sep. 5, 2007 in International Patent Application No. PCT/US2006/021021, 10 pages.
United States Patent and Trademark Office, Office Action mailed Apr. 20, 2007 in U.S. Appl. No. 10/651,162, 11 pages.
United States Patent and Trademark Office, Final Office Action mailed Mar. 7, 2007 in U.S. Appl. No. 12/037,025, 9 pages.
United States Patent and Trademark Office, Notice of Allowance mailed Jan. 10, 2007 in U.S. Appl. No. 10/650,959, 6 pages.
WIPO, U.S. International Preliminary Examining Authority, International Preliminary Report on Patentability mailed Nov. 30, 2006 in International Patent Application No. PCT/US2006/020975, 4 pages.
WIPO, U.S. International Search Authority, International Search Report and Written Opinion mailed Nov. 27, 2006 in International Patent Application No. PCT/US2006/020975, 6 pages.

United States Patent and Trademark Office, Office Action mailed Aug. 28, 2006 in U.S. Appl. No. 12/037,025, 7 pages.
United States Patent and Trademark Office, Office Action mailed Aug. 1, 2006 in U.S. Appl. No. 10/650,959, 8 pages.
United States Patent and Trademark Office, Final Office Action mailed May 3, 2006 in U.S. Appl. No. 12/037,025, 8 pags.
United States Patent and Trademark Office, Final Office Action mailed Jan. 10, 2006 in U.S. Appl. No. 10/650,959, 8 pages.
United States Patent and Trademark Office, Office Action mailed Aug. 9, 2005 in U.S. Appl. No. 12/037,025, 10 pages.
United States Patent and Trademark Office, Office Action mailed Jul. 14, 2005 in U.S. Appl. No. 10/650,959, 11 pages.
United States Patent and Trademark Office, Office Action mailed Sep. 29, 2004 in U.S. Appl. No. 12/037,025, 11 pages.
WIPO, U.S. International Search Authority, Written Opinion mailed Sep. 9, 2004 in International Patent Application No. PCT/202003/026924, 6 pages.
WIPO, U.S. International Search Authority, International Search Report mailed Jul. 7, 2004 in International Patent Application No. PCT/US2003/026924, 6 pages.
IP Australia, Examiner's Report mailed Apr. 18, 2011 in Australian Patent Application No. AU2006251938, 2 pages.

* cited by examiner

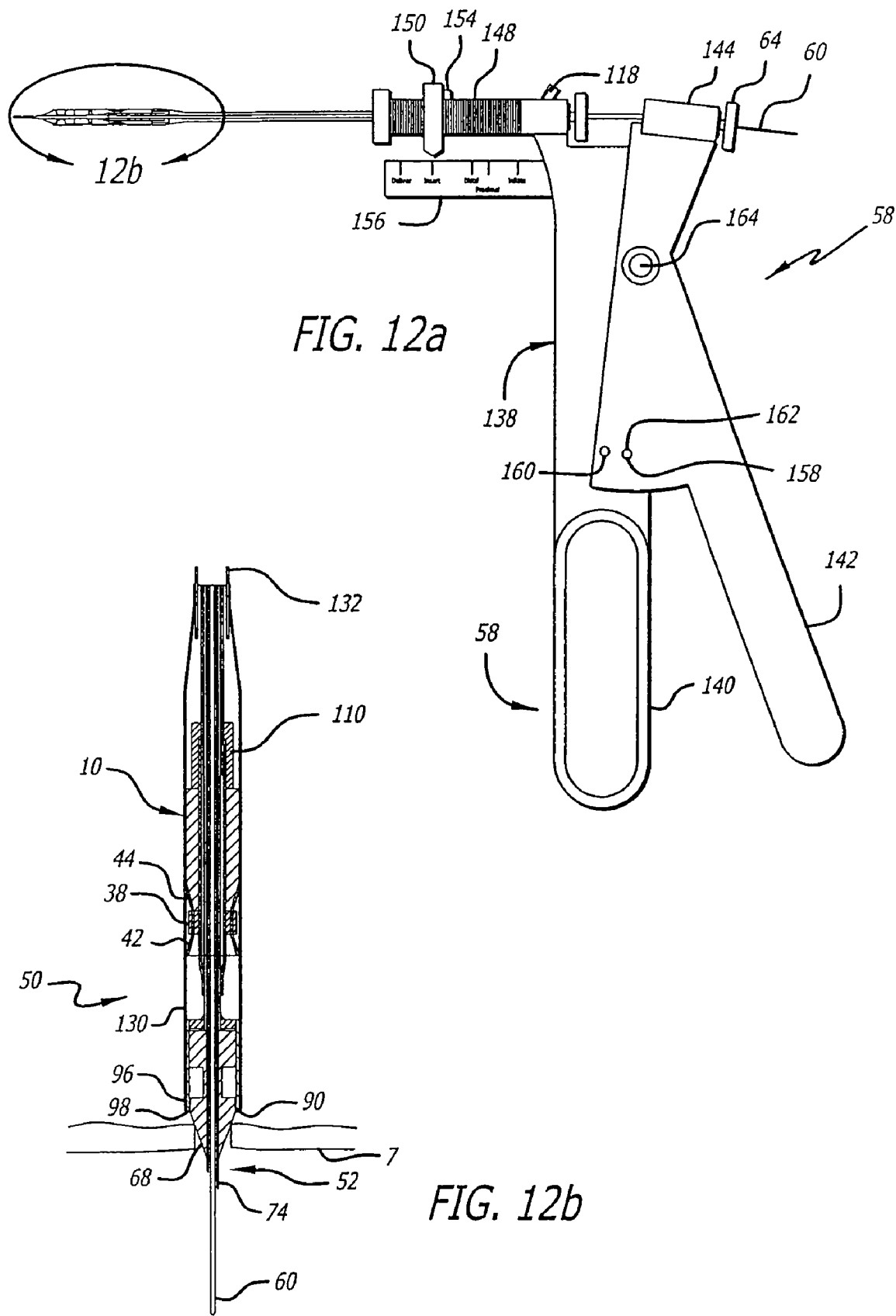

LEAFLET VALVE

CROSS REFERENCE TO RELATED APPLICATIONS

The present invention is a continuation of U.S. patent application Ser. No. 10/651,162 filed Aug. 28, 2003 now U.S. Pat. No. 7,335,218 entitled Delivery Device For Leaflet Valve, which claims benefit of U.S. Provisional Application Ser. No. 60/407,414, filed Aug. 28, 2002 entitled Mini-Valve Heart Valve Replacement, both of which are incorporated herein by reference.

BACKGROUND OF THE INVENTION

Blood vessel valves include flexible tissue leaflets that passively alternate between open and closed positions as the forces of a blood stream act upon them. As blood flows in a first direction, the leaflets are urged apart from each other, and allow the blood to pass. Between pulses, as the blood attempts to flow in a reverse direction, the blood acts upon upstream surfaces of the individual leaflets, causing the leaflets to move inwardly. As the leaflets move inwardly, the edges of the individual leaflets (two, in the case of bicuspid valves, and three in the case of tricuspid valves) abut against each other, effectively blocking the blood flow in the reverse direction.

Valves are also present within the heart. The heart contains four one-way valves that direct blood flow through the heart and into the arteries. Three of these valves, the aortic valve, the tricuspid valve, and the pulmonary valve, each have three leaflets. The fourth valve, the mitral valve, has two leaflets. By defining a direction in which blood can flow, these valves are responsible for the resulting pump effect a heart has on blood when the heart beats.

A number of diseases result in a thickening, and subsequent immobility or reduced mobility, of valve leaflets. Valve immobility leads to a narrowing, or stenosis, of the passageway through the valve. The increased resistance to blood flow that a stenosed valve presents eventually leads to heart failure and death.

Treating severe valve stenosis or regurgitation has heretofore involved complete removal of the existing native valve followed by the implantation of a prosthetic valve. Naturally, this is a heavily invasive procedure and inflicts great trauma on the body leading usually to great discomfort and considerable recovery time. It is also a sophisticated procedure that requires great expertise and talent to perform.

Historically, such valve replacement surgery has been performed using traditional open-heart surgery where the chest is opened, the heart stopped, the patient placed on cardiopulmonary bypass, the native valve excised and the replacement valve attached. More recently, it has been proposed to perform valve replacement surgery percutaneously, that is, through a catheter, so as to avoid opening the chest.

One such percutaneous valve replacement method is disclosed in U.S. Pat. No. 6,168,614 (the entire contents of which are hereby incorporated by reference) issued to Andersen et al. In this patent, the prosthetic valve is collapsed to a size that fits within a catheter. The catheter is then inserted into the patient's vasculature and moved so as to position the collapsed valve at the location of the native valve. A deployment mechanism is activated that expands the replacement valve against the walls of the body lumen. The expansion force pushes the leaflets of the existing native valve against the lumen wall thus essentially "excising" the native valve for all intents and purposes. The expanded structure, which includes a scaffold configured to have a valve shape with valve leaflet supports, is then released from the catheter and begins to take on the function of the native valve. As a result, a full valve replacement has been achieved but at a significantly reduced physical impact to the patient.

One particular drawback with the percutaneous approach disclosed in the Andersen '614 patent is the difficulty in preventing leakage around the perimeter of the new valve after implantation. Since it appears that the tissue of the native valve remains within the lumen, there is a strong likelihood that the commissural junctions and fusion points of the valve tissue (as pushed against the lumen wall) will make sealing of the prosthetic valve around the interface between the lumen and the prosthetic valve difficult. Furthermore, in some patients, the deflection of the leaflets against the lumen walls could potentially obstruct the ostial openings of the lumen.

Although both the traditional open heart valve replacement surgery and the newer percutaneous valve replacement surgery replace a native valve in entirely different ways and both have their drawbacks, the paradigm of these two approaches is identical: Render the native valve useless, either through excision (open heart) or immobilization (percutaneous), and then implant a completely new replacement prosthetic valve to take over. In other words, both approaches rely entirely on the premise that the native valve must be entirely replaced (physically or functionally) by an entirely new prosthetic valve.

In contravention of the prior art, the present invention introduces an entirely different paradigm to valve replacement surgery, something neither taught nor contemplated by the open heart approach or the percutaneous approach (e.g., U.S. Pat. No. 6,168,614) and something that largely avoids the drawbacks associated with both. More specifically, the present invention is premised on leaving the native valve in place, not on its excision or immobilization, and then utilizing the native valve as a platform for actually treating the diseased valve. This is a wholly new approach to treating diseased valves.

For example, in one embodiment of the invention, the physician diagnoses that the patient has a stenotic valve and then percutaneously mounts a plurality of small "leaflet valves" or "mini-valves" on one or more of the diseased native valve leaflets. In other words the native valve and its leaflets are used as a planar surface or a type of "bulkhead" on which new mini leaflet valves are mounted. The native valve remains in place but valve disfunction is remedied due to the presence of these new leaflet valves. As a result, the diseased valve is successfully treated without the complication associated with removing the native valve.

This leads to a much simpler and safer approach as compared to the prior art. It avoids the invasive nature of the open heart approach and avoids the sealing and ostial blockage problems of the percutaneous approach.

BRIEF SUMMARY OF THE INVENTION

The present invention relates to the treating of narrowed, stiff or calcified heart valves. The aforementioned problems with present treatment methods are addressed by treating the targeted valve leaflets individually, rather than replacing the entire valve using an open-heart or a percutaneous procedure. That is, in the present method, the rigid heart valve leaflet is treated by introducing small prosthetic valves into the leaflet itself.

The present invention includes a method of treating the individual leaflets of a targeted heart valve that includes installing one or more small, one-way valves into the targeted leaflets. These smaller valves can be placed in the leaflet using catheter systems, obviating the need for opening the heart or great vessels, cardiopulmonary bypass, excision of the diseased valve, and a thoracotomy. Additionally, multiple small valve placements might reduce the long-term risks associated with a complete prosthetic valve, because failure of an individual valve will not necessarily lead to cardiac failure. The remaining small valves and remaining healthy native valves might be sufficient to sustain life.

One aspect of the present invention provides a method of placing small valves through a target valve that involves puncturing the target valve and pushing the miniature valve through the target valve tissue. The valve is then anchored in place using a variety of mechanisms including tabs, riveting of the valve housing, spines, friction placement or the use of a fixation cuff.

Another aspect of the present invention provides a variety of valve implant mechanisms constructed and arranged for placement in a target valve leaflet. The valve implant mechanisms include a valve housing that operably houses a valve mechanism such as a duckbill valve, a tilting check valve, a ball and cage valve, or a hinged leaflet valve or a valve using tissue leaflets. The valve implant may also include an anchoring mechanism such as tabs, spines, threads, shoulders, or a deformable housing.

The present invention also provides a device useable to remove a section of the target valve, without damaging the surrounding valve tissue, and inserting a valve implant into the void left in the target valve. The device is contained within a catheter such that a valve implant insertion procedure can be accomplished percutaneously. Preferably, this delivery system is constructed and arranged to be placed through a 14 French catheter, traverse the aorta, land on a targeted leaflet such as one of the leaflets of the aortic valve, puncture the leaflet at a predetermined spot, cut a hole on the order of 4 mm in diameter, capture and remove any cut tissue, place a radially compressed one-way valve including a attachment cuff made of a shape memory alloy material (e.g., Nitinol) and a stainless steel sizing ring into the leaflet hole, securely attach the valve assembly to the leaflet, dilate the hole and the valve assembly to a precise final diameter, such as 8 mm, using a balloon, and be retracted leaving the valve assembly in place in the leaflet.

BRIEF DESCRIPTION OF THE DRAWINGS

FIG. 5b is a detailed sectional view of the distal end of the delivery system of FIG. 5a;

FIG. 9a is a detailed sectional view of the handle of the delivery system of the present invention;

FIG. 9b is a side elevation of the handle of FIG. 9a;

FIG. 10a is a side elevation of the handle of the present invention in a "Deliver" position;

FIG. 10b is a sectional view of the distal end of the delivery system of the present invention when the handle is in the "Deliver" position of FIG. 10a;

FIG. 11b is a sectional view of the distal end of the delivery system of the present invention when the handle is in the "Insert" position of FIG. 11a;

FIG. 12a is a side elevation of the handle of the present invention in a "Cut" position;

FIG. 12b is a sectional view of the distal end of the delivery system of the present invention when the handle is in the "Cut" position of FIG. 12a;

FIG. 14b is a sectional view of the distal end of the delivery system of the present invention when the handle is in the "Distal" position of FIG. 14a;

FIG. 15b is a sectional view of the distal end of the delivery system of the present invention when the handle is in the "Proximal" position of FIG. 15a;

DETAILED DESCRIPTION OF THE INVENTION

Figure 1:
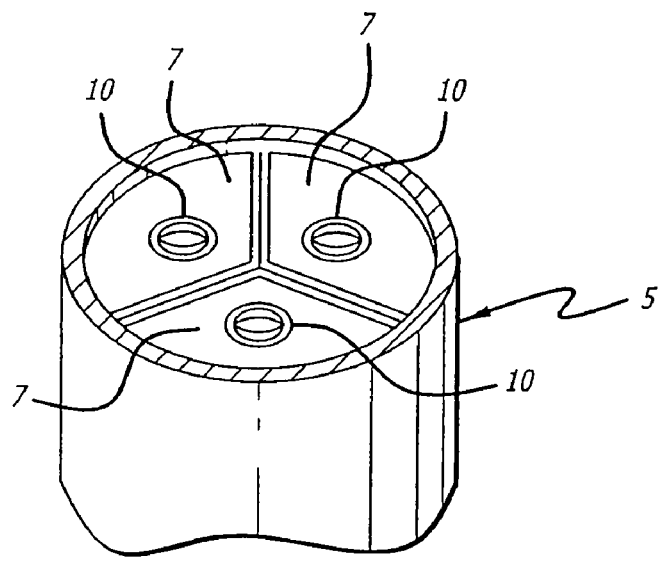
FIG. 1 is a perspective view of three valve implants of the present invention installed in the leaflets of a tricuspid valve.

Referring now to the Figures, and first to FIG. 1, there is shown a native tricuspid valve 5 with a valve implant 10 of the present invention installed in each of the three leaflets 7 of the tricuspid valve 5. The valve implants 10 are shown in an open position to demonstrate that blood is allowed to flow through the valve implants 10, in one direction, even though the native tricuspid valve 5 remains closed. These valve implants 10 would similarly work with a native bicuspid valve, unicuspid valve or quadracuspid valve.

Figure 2:
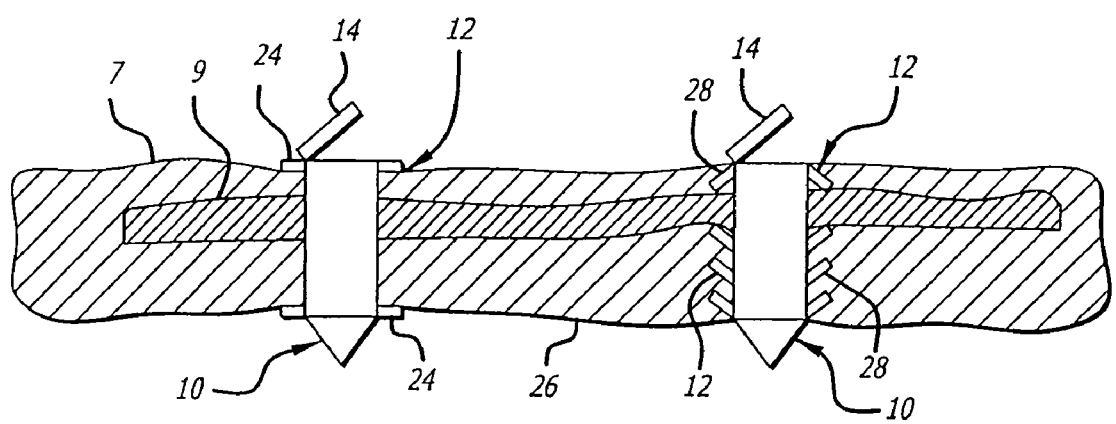
FIG. 2 is a side elevation of two valve implants of the present invention installed in a stenotic leaflet.

FIG. 2 demonstrates the positioning of a valve implant 10 in a native leaflet 7. The leaflet 7 is shown as having calcified tissue 9, characteristic of a stenosed valve. Notably, the valve implants 10 have been inserted through the calcified tissue 7. Also notable is that there may be more than one valve implant 10 inserted into a single leaflet 7 if additional flow capacity is desired. Alternatively, though not shown, the valve implant 10 may be installed between the leaflets 7. This configuration is especially feasible in heavily stenosed valves that have relatively immovable leaflets. Such leaflets may be fully or partially fused together. The valve implants generally comprise an anchoring mechanism 12 and a valve mechanism 14.

FIGS. 3-5 illustrate several embodiments of the valve implants 10 of the present invention. In FIGS. 3a-f, a family of valve implants 10 is provided that are characterized by a rigid housing 16 with a self-tapping tip 18. The valve implants 10 of FIGS. 3a-f include a variety of valve mechanisms 14 and anchoring mechanisms 12.

Figure 3A:
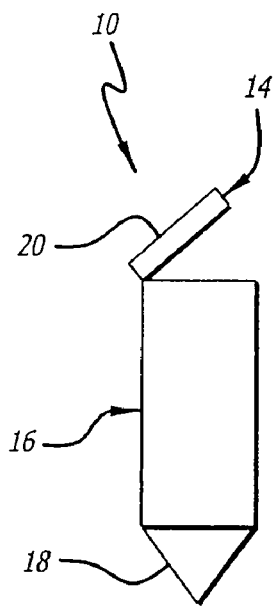
FIGS. 3a-f are side elevations of various embodiments of the valve implant of the present invention.
Figure 3B:
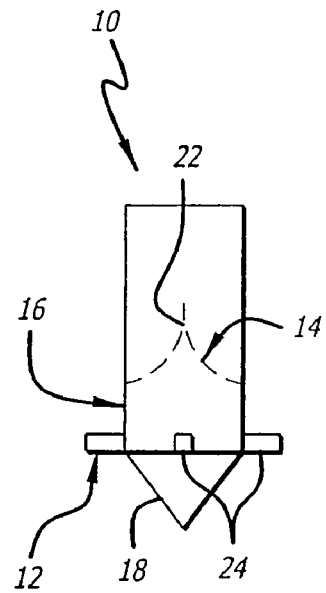
Figure 3C:
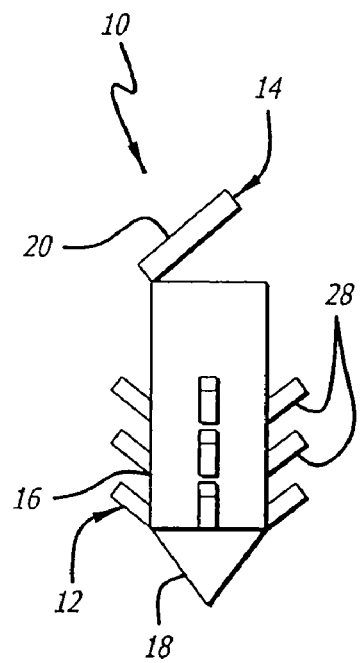
Figure 3D:
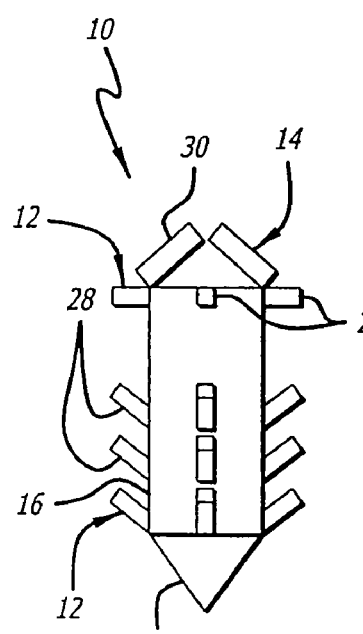

The valve implant 10 of FIG. 3a, as well as those of FIGS. 3c and 3d, has a valve mechanism 14 that comprises a single flap 20, hinged on one side, that acts against the rigid housing 16 to prevent flow in a reverse direction. A benefit of this valve design is ease of construction. The valve implant 10 of FIG. 3a also uses the friction between the rigid housing 16 and the native heart leaflet 7 (FIG. 2) as an anchoring mechanism to hold the valve implant 10 in place. The pointed tip 18 allows the valve implant 10 to be urged through, or twisted through, the native heart leaflet without the need for cutting a hole in the leaflet prior to installing the valve implant 10. Thus, in certain cases, there is sufficient gripping power between the housing 16 and the leaflet 7 to hold the housing 16 in place. This holding power may be increased by providing a textured surface (not shown) on the housing 16, or selecting a housing material, such as a mesh or stiff fabric, that allows a controlled amount of ingrowth, sufficient to secure the valve implant 10, but not so much as to cause a flow hindrance within the valve implant 10.

The valve implant 10 of FIG. 3b has a valve mechanism 14 that comprises a pair of members constructed and arranged to form a duckbill valve 22. The duckbill valve 22 operates in a similar way to a tricuspid or bicuspid valve. When fluid flows through the valve in a desired direction, each of the members of the duckbill valve 22 move apart from each other. When the flow reverses, such as during diastole, the fluid forces the members of the duckbill valve 22 together, closing the valve 10.

Also included in the valve implant 10 of FIG. 3b is an anchoring mechanism 12. The anchoring mechanism 12 generally comprises a plurality of radially extending posts 24. These posts 24 act against an upstream side 26 (FIG. 2) of the leaflet 7, thereby counteracting systolic pressure from the blood stream.

The valve implant 10 of FIG. 3c includes a single flap 20 valve mechanism 14 and an anchoring mechanism 12 that includes a plurality of angled barbs 28. The barbs 28 are located near the upstream side of the valve implant 10 and are angled back toward the downstream side. The angled barbs 28 may provide increased gripping power, especially if more than one row, such as shown in FIG. 3c, are provided. Because one or more of the rows of barbs 28 will be located within the leaflet 7 when the valve implant is in place, the barbs 28 provide resistance to movement in both directions, and may stimulate ingrowth.

The valve implant 10 of FIG. 3d provides a combination of many of the features already discussed. The valve 10 has an anchoring mechanism 12 that includes both posts 24, on the downstream side to prevent valve movement in the upstream direction, and angled barbs 28 on the upstream side of the valve 10. The valve mechanism 14 demonstrates another valve design. The valve mechanism is an outside-hinged dual flap valve 30. The individual flap members rotate about their outer edges when influenced by fluid flow.

Figure 3E:
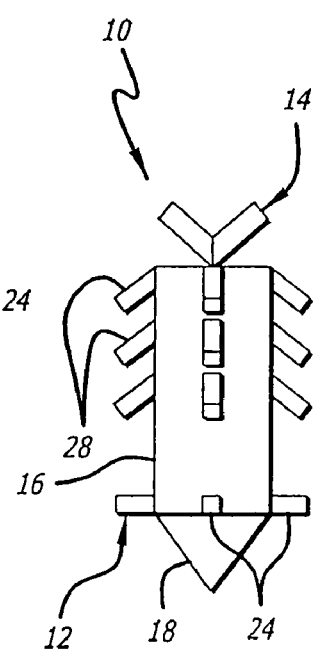

FIG. 3e shows a valve implant 10 with a valve mechanism 14 that uses an inside-hinged dual flap valve 32, with individual flap members that rotate about their inner edges when influenced by fluid flow. The valve implant 10 combines upstream posts 24 with upstream-angled barbs 28 on the downstream side of the valve implant 10.

Figure 3F:
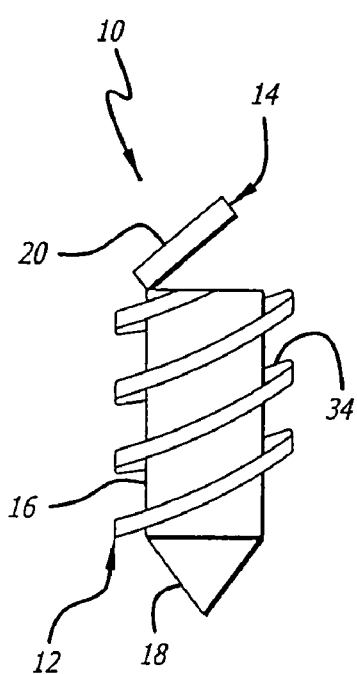

The valve implant 10 shown in FIG. 3f combines a single flap 20, as a valve mechanism 14, with an anchoring mechanism 12 that uses an external helical thread 34 to anchor the valve implant 10 to a valve leaflet 7. The helical thread 34 provides resistance to movement in both the upstream and downstream directions. The helical thread 34 also provides a self-tapping action when the valve implant 10 is being screwed into place in a leaflet 7.

One skilled in the art will realize that any of the aforementioned anchoring mechanisms 12 and valve mechanisms 14 may be combined in a single valve implant 10. For example, the valve implants 10 shown in FIG. 2 include upstream and downstream posts 24 as well as upstream and downstream angled barbs 28.

Figure 4A:
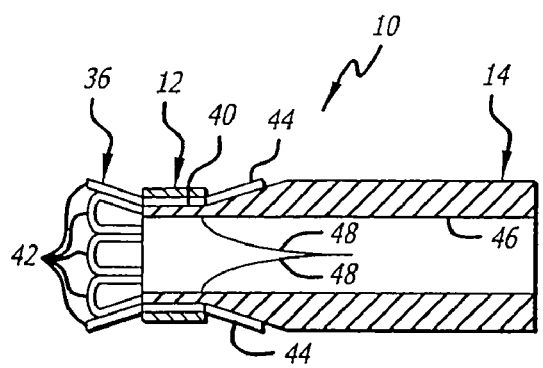
FIG. 4a is a detailed sectional view of a preferred embodiment of the valve implant of the present invention in a compressed or folded state.
Figure 4B:
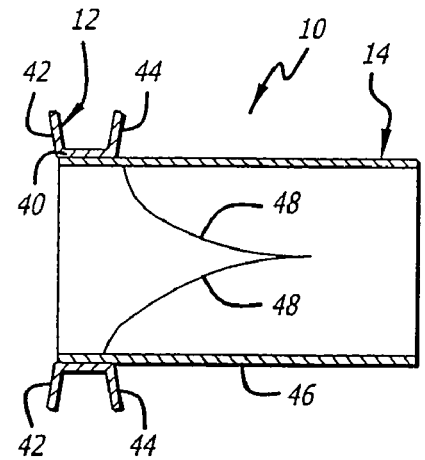
FIG. 4b is a detailed sectional view of the valve implant of FIG. 4a in an expanded state.
Figure 4C:
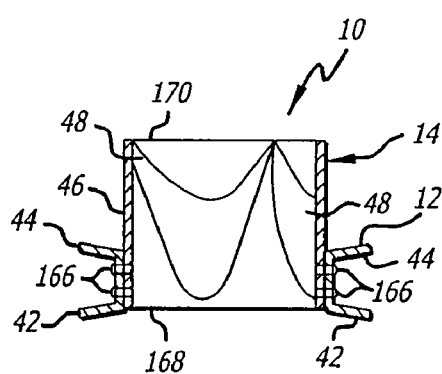
FIGS. 4c-f are sectional views of alternative configurations of the preferred valve implant of the present invention.
Figure 4D:
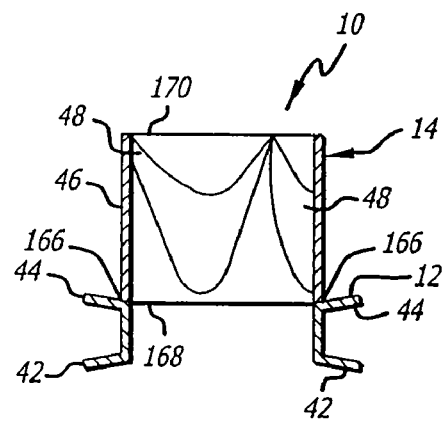
Figure 4E:
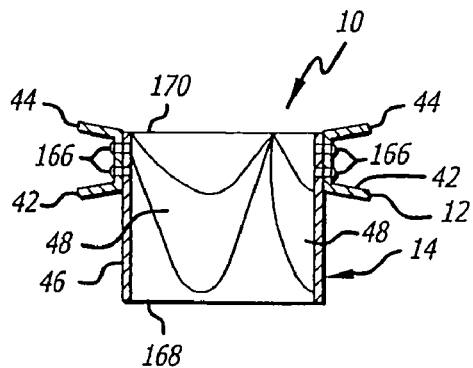
Figure 4F:
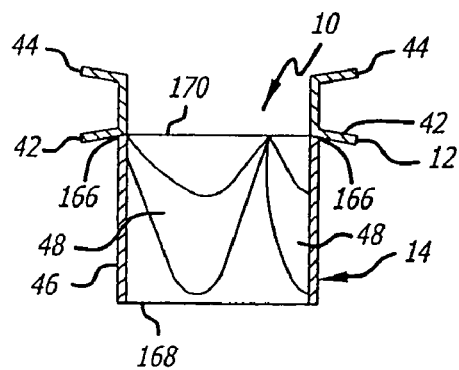

A preferred embodiment of the valve implant 10 of the present invention is shown in FIGS. 4a and 4b. The valve implant 10 is expandable from the compressed configuration shown in FIG. 4a, to the expanded configuration shown in FIG. 4b. The valve implant 10 is constructed and arranged to fit within a catheter when in the compressed configuration. Compression may be accomplished radially, helically, longitudinally, or a combination thereof. Preferably, the compression of the valve implant 10 is radial.

Like the aforementioned embodiments of the valve implants 10, the valve implant 10 of FIG. 4 generally includes an anchoring mechanism 12 and a valve mechanism 14. The anchoring mechanism 12 generally comprises a cuff 36 and a sizing ring 38. The cuff 36 is preferably constructed of Nitonol and has a middle portion 40 a set of radially expanding distal legs 42 and a set of radially expanding proximal legs 44.

In the compressed state, the legs 42 and 44 are somewhat aligned with the middle portion 40 to allow the cuff 36 to be compressed into a catheter, preferably a 14 French catheter. The cuff 36 is either expandable or self-expanding. Upon release from the catheter, the legs 42 and 44 fold outwardly until they radiate from the middle portion 40 at approximately right angles to the longitudinal axis of the cuff 36. The legs 42 and 44 are designed to act against the upstream and downstream sides, respectively, of a valve leaflet, sandwiching the leaflet therebetween and anchoring the cuff 36 to the leaflet.

The anchoring mechanism 12 of the valve implant 10 shown in FIGS. 4a and 4b also includes a sizing ring 38. The sizing ring 38 is preferably a stainless steel stent that circumjacently surrounds the middle portion 40 of the cuff 36. The sizing ring 38 is constructed and arranged to expand with the cuff 36 until a predetermined size is reached. Once the predetermined size is reached, the sizing ring 38 prevents further expansion by the cuff 36. Over expansion of the cuff 36 could render the valve mechanism 14 inoperable, cause calcified tissue to break away from the stenosed valve and become released into the blood stream, tear the leaflet tissue, or weaken the cuff 36.

The valve mechanism 14 includes a sleeve 46 and one or more valve members 48. The sleeve 46 may be rigid or flexible, but it is preferably flexible. More preferably, the sleeve 46 is constructed of any sufficiently flexible material capable of withstanding the environment to which it will be subjected, including but not limited to, any mammalian tissue, including human or pig tissue, vertebrate tissue, or a polymer or other synthetic material. The valve members 48 are shown as being duckbill valves but may be any of the aforementioned discussed valve designs.

Most preferably, the valve mechanism 14 comprises an intact harvested valve from an animal, such as pig, and is taken from an appropriate location such that the expanded, original size is suitable for use in the leaflets of the stenotic valve being treated. The harvested valve is sutured or otherwise attached to the inside surface of the cuff 36. In operation, the valve implant 10 is compressed such that it can be placed in a small catheter for percutaneous delivery. At the time of delivery, the valve implant 10 is attached to a stenotic leaflet and radially expanded to its functional diameter. Prior to, or during expansion, the distal and proximal legs 42 and 44 expand radially, allowing the cuff 36 to create a strong bulkhead-like fitting on both sides of the leaflet. After attachment is made to the leaflet, the cuff 36, sizing ring 38, and the valve mechanism 14 are radially expanded to the functional diameter of the valve implant 10. During this expansion, the sizing ring 38 exhibits plastic deformation until it achieves the maximum diameter, at which point the sizing ring 38 resists further expansion.

FIGS. 4c-4f depict alternative configurations for the preferred valve implant 10. The valve implant 10 in FIG. 4c has a sleeve 46 attached to the anchoring mechanism 12 with two rows of sutures 166 and is configured so an upstream edge 168 of the sleeve 46 is roughly aligned with the distal legs 42 of the anchoring mechanism 12. The valve implant 10 in FIG. 4d has a sleeve 46 attached to the anchoring mechanism 12 with one row of sutures 166 and is configured so the upstream edge 168 of the sleeve 46 is roughly aligned with the proximal legs 44 of the anchoring mechanism 12. The valve implant 10 in FIG. 4e has a sleeve 46 attached to the anchoring mechanism 12 with two rows of sutures 166 and is configured so the downstream edge 170 of the sleeve 46 is roughly aligned with the proximal legs 44 of the anchoring mechanism 12. The valve implant 10 in FIG. 4f has a sleeve 46 attached to the anchoring mechanism 12 with one row of sutures 166 and is configured so the downstream edge 170 of the sleeve 46 is roughly aligned with the distal legs 42 of the anchoring mechanism 12. The sleeve 46 may comprise a scaffold to which valve members 48 are attached, or the entire valve mechanism 14 may be a harvested tissue valve such as an aortic valve.

In one preferred embodiment, the valve implant 10 can be configured to include commissural support structure like a wireform stent as sometimes found in known standard sized prosthetic tissue valves. In such a configuration, the valve material will comprise a biologic tissue such as human pericardium or equine pericardium or small intestine submucousal tissue. In the present invention, the material must be thin enough to be compressed and perhaps folded so as to fit the valve implant 10 within the delivery system (described below). In a preferred embodiment, such tissue has a thickness of around 180 microns or less.

In another alternative embodiment, the cuff mechanism could be a torroidal shaped sack (not shown), similar in shape to a deflated inner tube, attached to the exterior surface of the base of the valve implant 10 and connected to a UV curable liquid polymer reservoir contained within the delivery catheter. The sack material is composed of an elastic material that can be radially expanded by a balloon angioplasty catheter or by the injection of the liquid polymer. The liquid adhesive contained within the sack can be transformed to a solid polymer through UV light activated cross-linking This sack, essentially empty, can be manipulated by the delivery catheter to straddle both sides or surfaces around the hole cut in the leaflet for receiving the valve implant 10. Once located, the sack can be enlarged by an underlying balloon catheter. Then, UV curable liquid polymer can be injected into the sack through the delivery catheter. Once filled with an adequate amount of a polymer and adjusted distally/proximally to form sufficient bulges on both sides of the valve leaflet, a UV light emission source, located within the delivery catheter near the bag is activated to wash the adhesive filled bag with UV curing light. Once hardened by the UV effect, the cuff maintains its enlarged size without balloon support.

Figure 24A:
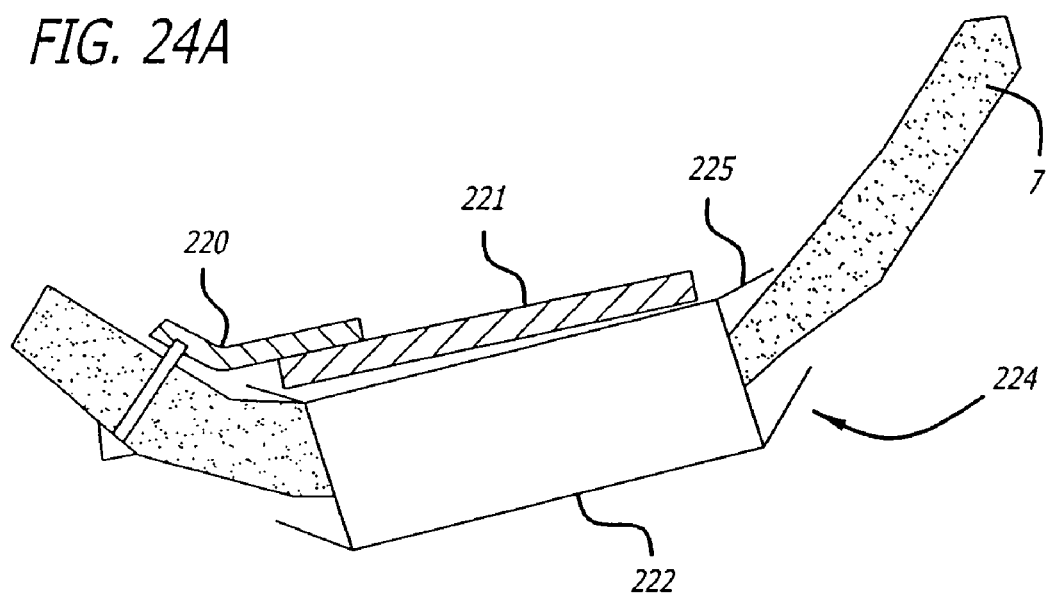
Figure 24B:
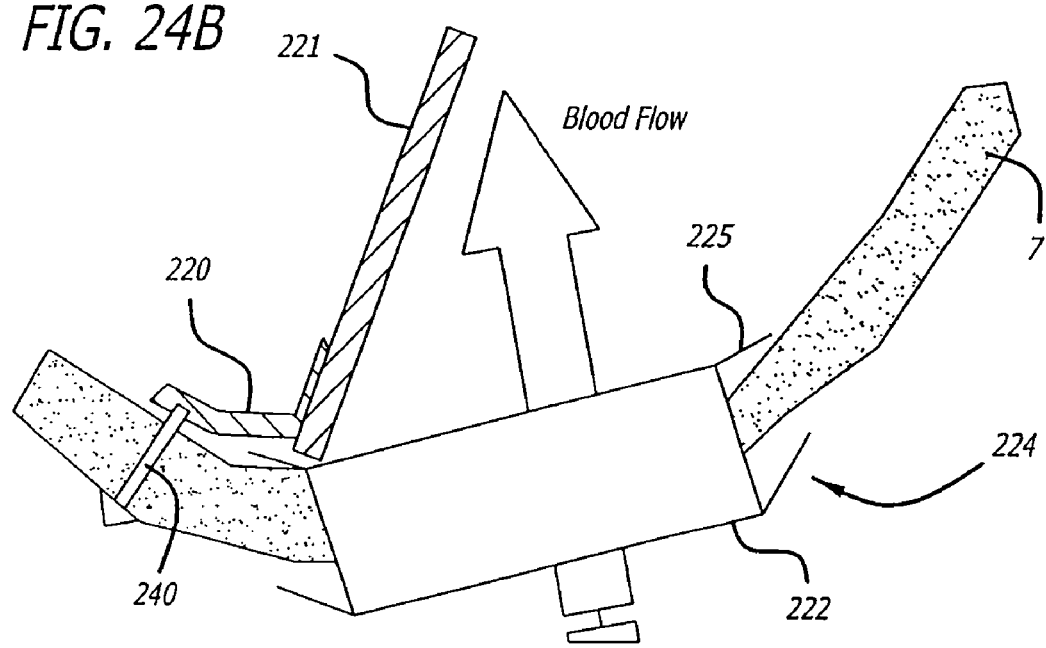

Referring to FIGS. 22A-24B, yet another embodiment of a valve implant 10 of the present invention is shown, this embodiment being a hinged valve. In this embodiment, the valve implant 10 comprises a valve "poppet" 221 that is connected to a valve leaflet 7 by an attachment mechanism 220 that operates much like a hinge. The valve poppet 221 pivots between a sealed and an unsealed condition around the pivot point of the attachment mechanism 220 according to the flow of blood (FIGS. 24A and 24B).

The poppet 221 or "mini-leaflet" can be comprised of any material sufficiently flexible to allow for the described movement yet sufficiently durable to withstand the environment. For example, the poppet 221 may made from materials such as biologic tissue, a polymer or a carbon based material. Moreover, the poppet 221 could be coated with tissue prom the patient, e.g., tissue from a patient's vein wall. The poppet material may include supporting internal structure and/or an outer ring to ensure the structural integrity of the poppet 221 during operation. The poppet can have a curved in order to better conform the poppet 221 to the contour of the native leaflet 7.

In this regard, after a hole is created in the leaflet 7 (discussed below), the poppet 221 is pushed or screwed into the leaflet. It may be retained there by barbs or screw threads or by hooks or other types of retaining mechanisms.

The attachment mechanism 220 (FIGS. 22A-22B and 24A-24B), in a preferred embodiment, is a hinge. The hinge may fabricated from such materials as a polymer strip, a biologic tissue strip, a metal (e.g., stainless steel) strip or a pryolytic carbon material. Referring to FIGS. 24A and 24B, the hinged mechanism may be attached to the leaflet 7 tissue using a barbed spike 240.

In an optional embodiment of the invention shown in FIGS. 22A-24B, the valve implant 10 may also include a support ring 222 that is disposed around the inside perimeter of the hole that is cut in the leaflet 7 to receive the valve implant 10. The support ring 222 may serve to limit embolization and to enhance leaflet integrity (thereby avoiding prolapse). The support ring 222 could be deployed into the hole either with an expanding balloon or it could be mechanically deployed using a mechanical spreader.

Referring to FIGS. 23A-24B, the optional support ring 222 may include struts 224, 225 that serve to capture the edges of the leaflet 7 in the hole so as to support and retain the support ring 220 at the site.

Catheter Delivery System

Figure 5A:
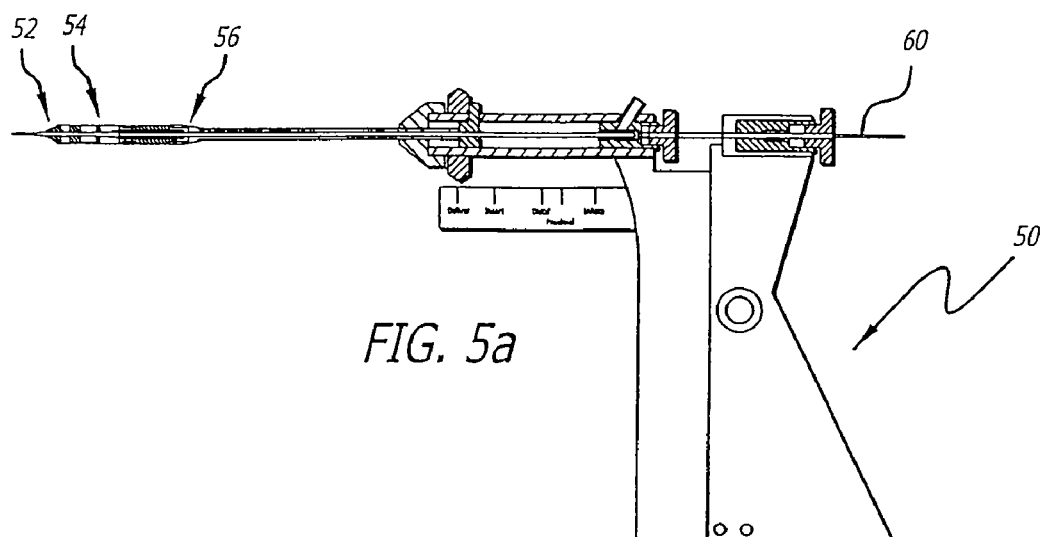
FIG. 5a is a sectional view of an embodiment of the delivery system of the present invention.
Figure 5B:
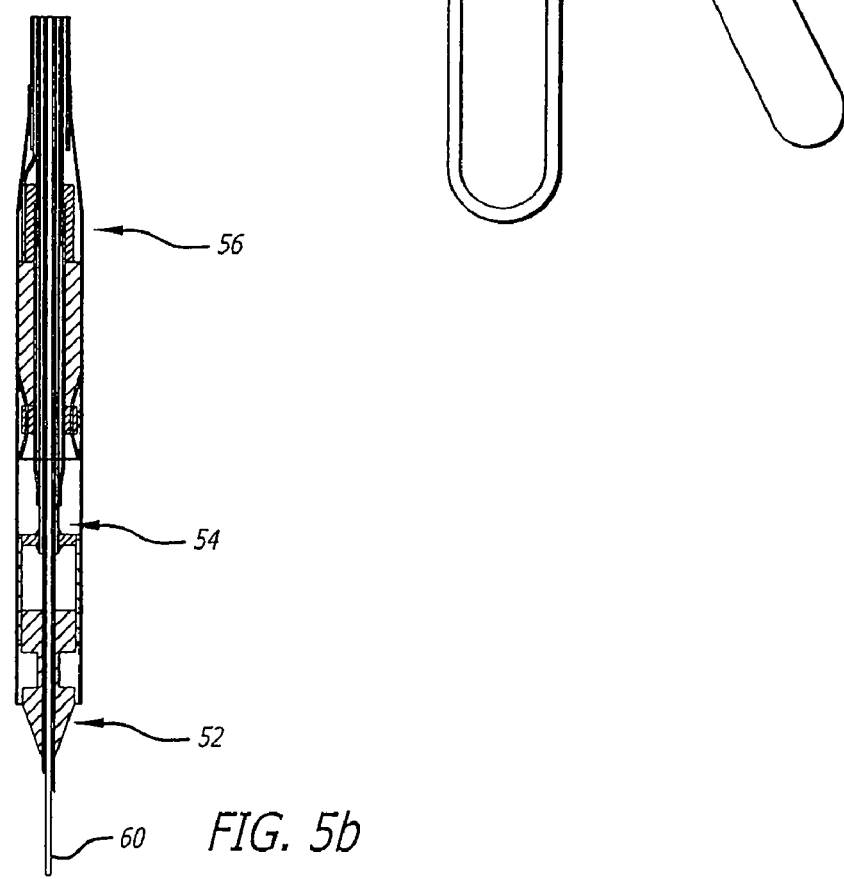

Referring now to FIGS. 5a and 5b, there is shown a preferred embodiment of a catheter delivery system 50 of the present invention. The catheter delivery system 50 generally comprises a leaflet capture catheter 52, a delivery catheter 54, a catheter sheath 56, and a handle 58. The catheter delivery system 50 is preferably constructed and arranged for use with a guidewire 60.

Figure 6:
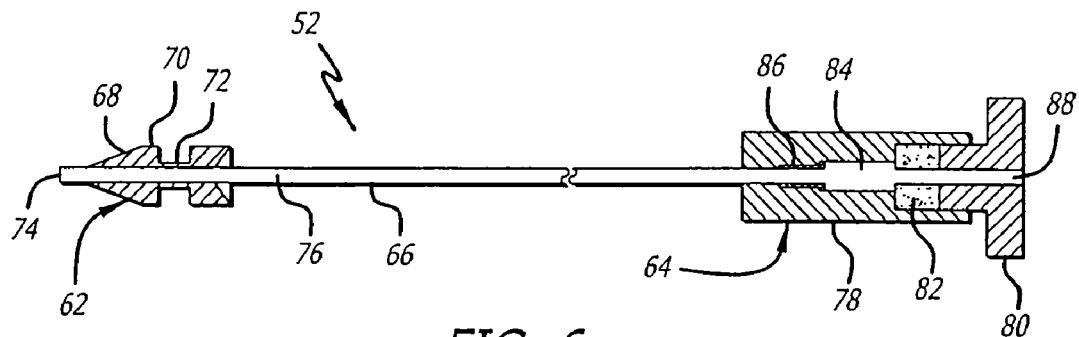
FIG. 6 is a sectional view of the leaflet capture catheter of the present invention.

As best seen in FIG. 6, the leaflet capture catheter 52 includes a cutter die 62 connected to a hemostatic hub 64 with a cannula 66. The cutter die 62 may be of unitary construction and includes a conical distal end 68 that increases in radius proximally until a flat 70 is reached. Proceeding proximally, the flat 70 ends abruptly to form a capture groove 72. At the proximal end of the capture groove 72, the cutter die 62 returns to approximately the same diameter as the flat 70. The purpose of the cutter die 62 is to "grab" tissue that resiliently "pops" into the capture groove 72. Once in the capture groove 72, the tissue is held in place as a cutter 90 (explained below) cuts through the tissue.

One skilled in the art will realize that alternatives could be used instead of a cutter die 62. For example, the cutter die 62 could be replaced with a balloon, constructed and arranged to be inflated on the upstream side of the leaflet 7 (or both sides of the leaflet to capture the tissue) and sized to fit within the cutter 90. A second balloon could also be arranged to be inflated on the downstream side of the leaflet, such that the leaflet is captured between the two balloons. The balloon concept, though arguably more complicated and expensive, may prove useful in situations where a cut needs to be made in tissue that has lost the resiliency needed to "pop" into the capture groove 72 of the cutter die 62. Other devices, such as barbs and clamps, are also envisioned to act in this manner.

The cannula 66 connects with the cutter die 62 and the hemostatic hub 64. At the distal end of the cannula 66 is a needle tip 74. The needle tip 74 is angled to form a sharp point usable to puncture tissue. The cannula 66 includes a lumen 76 extending the length thereof. This lumen 76 is used to accommodate a guidewire 60 (FIG. 5).

The hemostatic hub 64 allows the leaflet capture catheter 52 to be removably attached to the handle 58. The hemostatic hub 64 includes a body 78, a threaded knob 80, and an elastomeric seal 82. The body 78 defines an interior cavity 84 that is shaped to receive and hold a cannula hub 86 that is attached to a proximal end of the cannula 66. The interior cavity 84 is also shaped to receive the elastomeric seal 82, which is compressed between the threaded knob 80 and the body 78. The interior cavity 84 is partially internally threaded to receive the external threads of the threaded knob 80. The threaded knob 80 defines a guidewire port 88 that aligns with the interior cavity 84 and the lumen 76 of the cannula 66 so that a continuous port is available for the guidewire 60 to extend the length of the leaflet capture catheter 52. When a guidewire 60 is inserted through the guidewire port 88, the threaded knob 80 and the elastomeric seal 82 act together as a hemostatic valve. When the threaded knob 80 is rotated to compress the elastomeric seal 82, the elastomeric seal 82 swells inwardly, until it forms a blood-tight seal around the guidewire 60. The cannula 66 and the hub 64 are constructed and arranged to carry the tensile force generated during a hole cutting procedure, discussed in detail below.

Figure 7A:
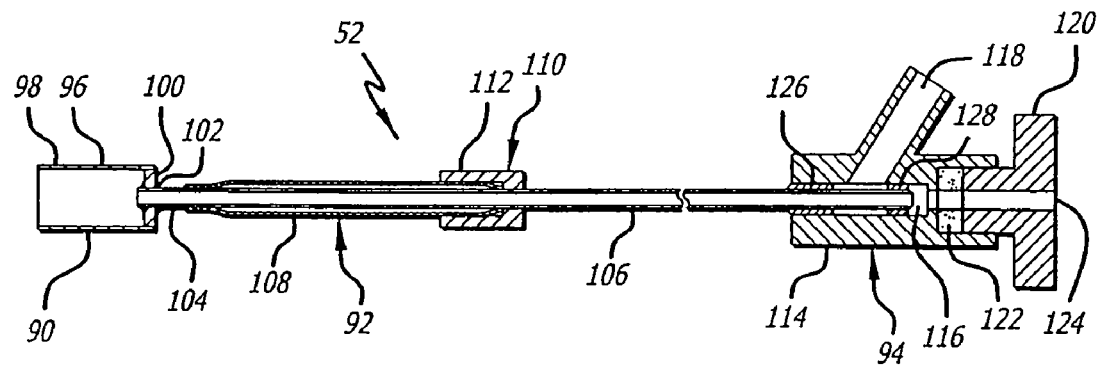
FIG. 7a is a sectional view of the delivery catheter of the present invention.
Figure 7B:
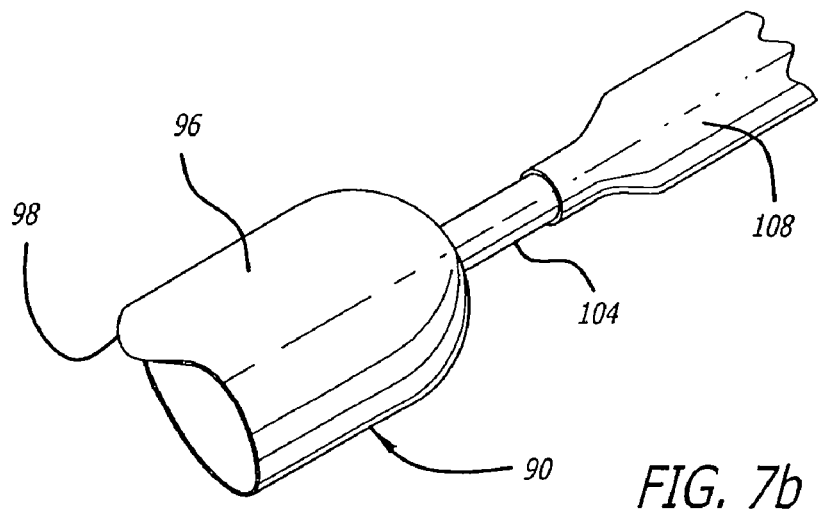
FIG. 7b is a perspective view of an alternative cutter of the present invention.

The leaflet capture catheter 52 is slidingly and coaxially contained within the delivery catheter 54. The delivery catheter 54 is best shown in FIG. 7a, and includes a cutter 90, a balloon catheter 92, and a delivery catheter hub 94. The cutter 90 is constructed and arranged to act with the cutter die 62 (FIG. 6) to cut tissue. The cutter 90 includes a cutter drum 96 that is a sharpened cylindrical blade having a cutting tip 98. The cutter tip 98, as shown in FIG. 7a, lies in a plane that is substantially perpendicular to a longitudinal axis of the delivery catheter. However, an alternative embodiment of the cutter drum 96, shown in FIG. 7b, may provide increased cutting power. The cutter drum 96 in FIG. 7b has a curved, non-planar cutting tip 98. Preferably, the cutter drum 96 is sized to cut a hole having a diameter of approximately 4 mm through a leaflet. The cutter drum 96 has a cutter bulkhead 100 at its proximal end that is attached to the balloon catheter 92 with an adhesive 102. Other suitable attachment means for attaching the cutter drum 96 to the balloon catheter 92 include threads, welds, unitary construction and the like. To cut tissue, the cutter die 62 is pulled within the cutter drum 90. Thus, the balloon catheter 92, and the adhesive 102 fixing the bulkhead 100 to the balloon catheter 92, must be able to carry the compressive force that results from opposing the equal and opposite tensile force applied to the leaflet capture catheter 52.

The balloon catheter 92 generally includes an inner tube 104 extending distally and proximally from within an outer tube 106. A balloon 108 is connected at a distal end to the outside of the inner tube 104 and at a proximal end to the outside of the outer tube 106. The outside diameter of the inner tube 104 is smaller than the inside diameter of the outer tube 106, such that a fluid passageway is formed therebetween for inflation of the balloon 108. A flexible valve stop 110 is attached to the outer tube 106 just proximal of the proximal end of the balloon 108. The valve stop 110 has a flexible sleeve 112 that extends distally over the proximal end of the balloon 108. The function of the valve stop 110 is to prevent proximal movement of the valve implant 10 during delivery. The valve implant 10, as will be seen below, will be placed over the balloon 108, distal of the valve stop 110. The flexible sleeve 112 allows the balloon to inflate while maintaining a desired positioning of the valve implant 10. The inner tube 104 has an inner diameter large enough to accommodate the cannula 66 of the leaflet capture catheter 52. A proximal end of the balloon catheter 92 is attached to the catheter hub 94.

The catheter hub 94 includes a catheter hub body 114 that defines an inner cavity 116 and a balloon inflation port 118. The proximal end of the inner cavity 116 has internal threads to receive an externally threaded knob 120. An elastomeric seal 122 resides between the threaded knob 120 and the catheter hub body 114. The threaded knob 120 defines a capture catheter port 124 that aligns with the interior cavity 116 of the body 114 and the interior of the balloon catheter 92 so that the leaflet capture catheter 52 may pass therethrough.

The balloon catheter 92 is attached to the catheter hub 94 in such a manner that fluid introduced into the balloon inflation port 118 will flow between the outer tube 106 and the inner tube 104 to inflate the balloon 108. The outer tube 106 is attached at its proximal end to the distal end of the interior cavity 116 of the catheter hub body 114. Preferably, an adhesive 126 is used to connect the outer tube 106 to the interior cavity 116 of the catheter hub body 114 at a position distal of the balloon inflation port 118. The inner tube 104 extends proximally from the proximal end of the outer tube 108. The proximal end of the inner tube 104 is also attached to the interior cavity 116 of the catheter hub body 114. However, this connection is made at a position proximal of the balloon inflation port 118, preferably with an adhesive 128. Thus, fluid entering the balloon inflation port 118 is blocked from flowing in a proximal direction by the proximal adhesive 128. It is also blocked from traveling in a distal direction on the outside of outer tube 106 by the distal adhesive 126. Instead, the fluid is forced to flow between the inner tube 104 and the outer tube 106 in a distal direction toward the interior of the balloon 108.

Figure 8:
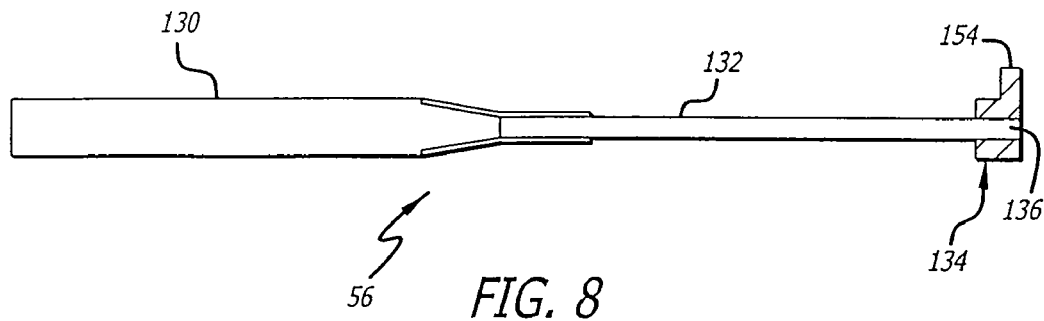
FIG. 8 is a sectional view of the sheath catheter of the present invention.

The leaflet capture catheter 52 and the delivery catheter 54 are slideably contained within the sheath catheter 56. Referring now to FIG. 8, it can be seen that the sheath catheter 56 includes a large diameter sheath 130 attached to a distal end of sheath tubing 132, which is attached at a proximal end to a sheath hub 134. The sheath hub 134 secures the sheath catheter 56 to the handle 58. The sheath hub 134 includes a tab 154, the function of which will be explained below. The sheath 130, sheath tubing 132, and the sheath hub 134, all define a delivery catheter port 136 that extends throughout the length of the sheath catheter 56. The large diameter sheath 130, is preferably a 14 French catheter, and sized to accommodate the cutter drum 96.

Figures 9A, 9B:
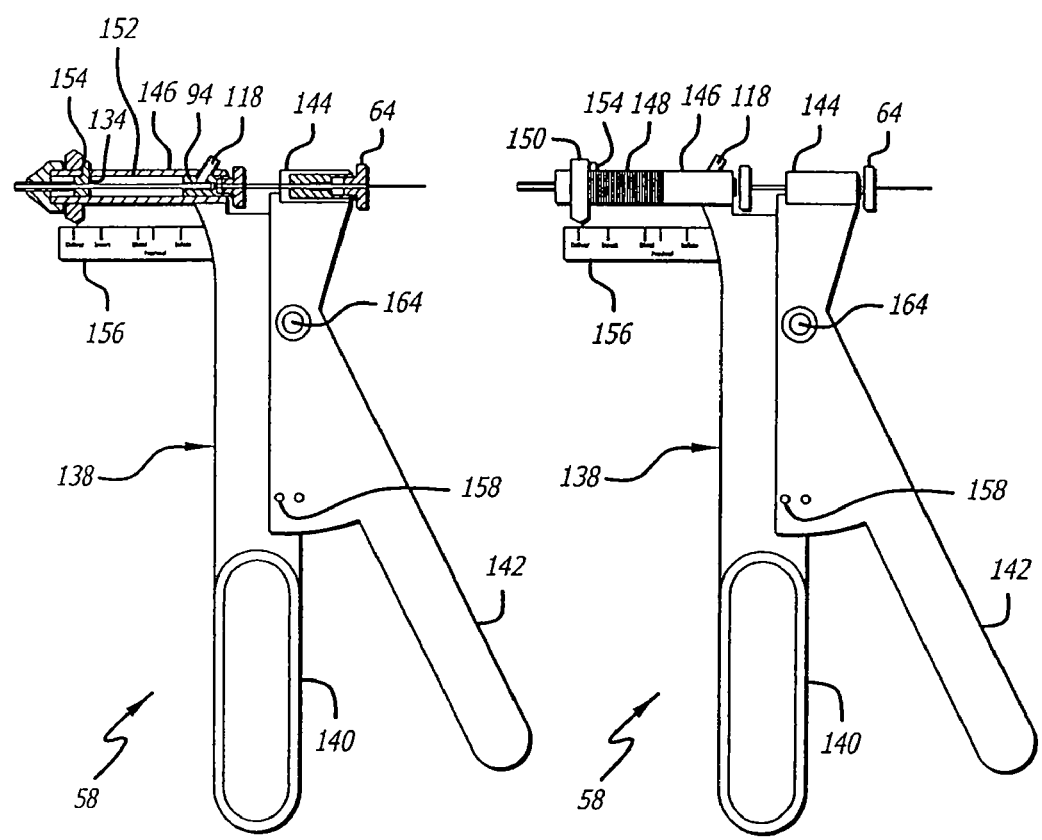

Referring now to FIGS. 9A and 9B, there is shown a preferred embodiment of the handle 58 of the present invention. The handle 58 includes a handle body 138 that defines at a bottom portion a figure grip 140. An actuator 142 is pivotally attached to the handle body 138 with a pivot pin 164. At the top of the actuator 142, is a leaflet capture catheter bracket 144. The leaflet capture catheter bracket 144 is constructed and arranged to hold the leaflet capture hemostatic hub 64. At a top portion of the body 138 there is defined a slotted chamber 146. The slotted chamber 146 is constructed and arranged to hold the delivery catheter hub 94 as well as the sheath hub 134. The slotted chamber 146 includes external threads 148 around which the sheath retraction nut 150 rides. At the top of the slotted chamber 146 there is defined a slot 152 through which the balloon inflation port 118 of the delivery catheter hub 94 and a tab 154 of the sheath hub 134 extend. Below the slotted chamber 146, a sheath retraction indicator 156 extends distally from the handle body 138. Preferably, the handle 58 includes a safety button 158 that prevents a physician from unintentionally depressing the actuator 142.

The handle 58 is thus constructed and arranged to slide the leaflet capture catheter 52 in a proximal direction relative to the sheath catheter 56 and the delivery catheter 54 when the actuator 142 is squeezed toward the finger grip 140, thereby pulling the hemostatic hub 64 in a proximal direction. The handle 58 is also constructed and arranged to slide the sheath catheter 56 proximally over the leaflet capture catheter 52 and the delivery catheter 54 when the sheath retraction nut 150 is rotated proximally. The operation of the handle 58 and the rest of the delivery system 50 are explained in more detail below.

Figure 19A:
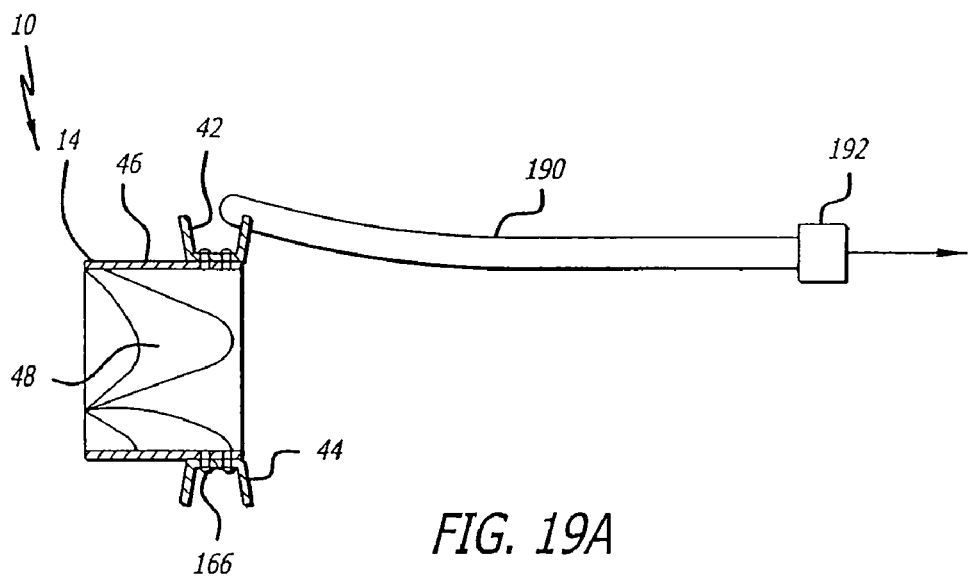
FIGS. 19A and 19B are cross-sectional views of a valve implant of the present invention in a deployed configuration.
Figure 19B:
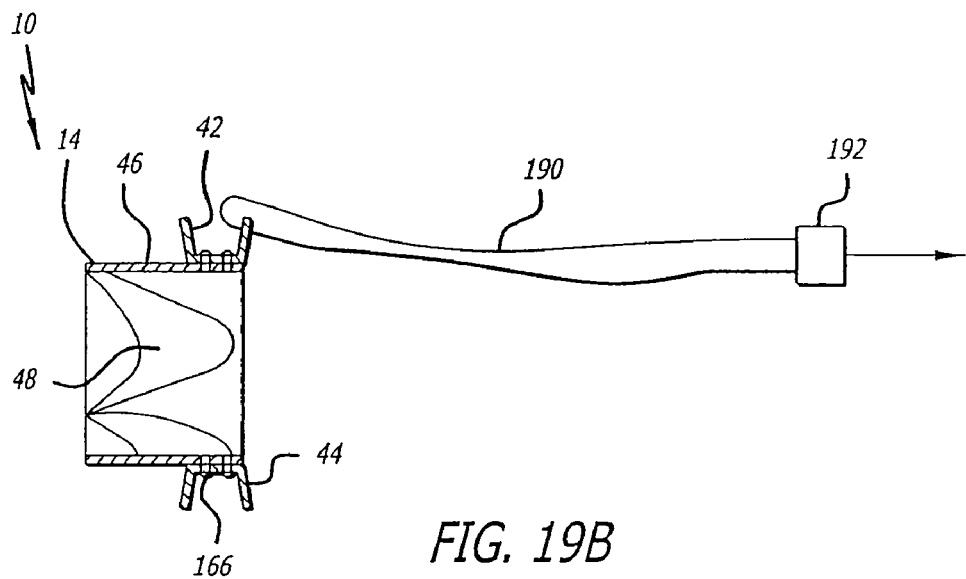
Figure 20:
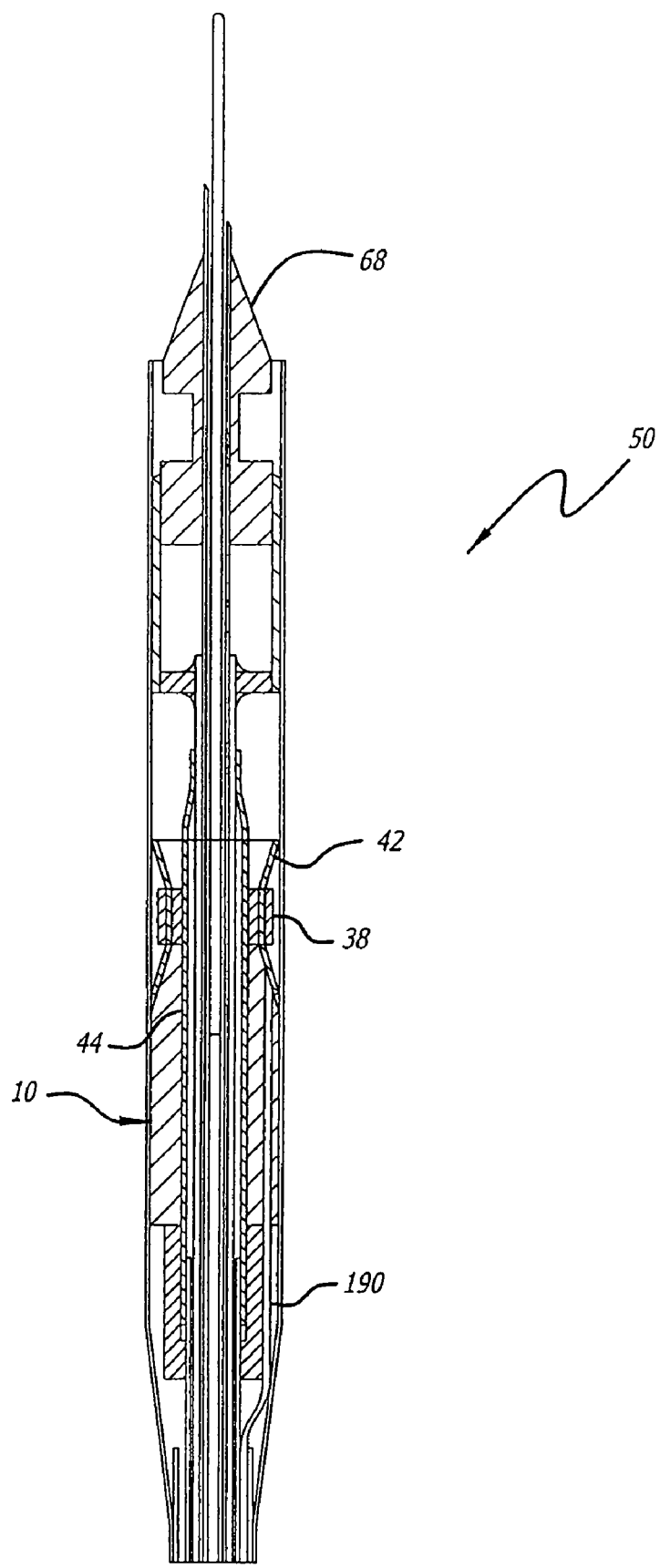
FIG. 20 is a cross-sectional view of a portion of a catheter delivery system in accordance with a preferred embodiment of the present invention.

Referring to FIGS. 19A, 19B and 20, in one embodiment of the present invention, the catheter delivery system 50 includes a tether 190 looped around the proximal legs 44 of the valve implant 10. The tether extends from the proximal legs 44 all the way through the catheter until both ends of the tether 190 are joined at a connector 192 that resides outside the catheter delivery system 50 near the handle. The tether 190 allows the user to retract the valve implant 10 from the valve placement site after it has been deployed from the catheter if it is determined that the deployment was improper or in the event a complication arises with after deployment.

For example, if after deployment, it is determined that placement of the valve implant 10 is incorrect, the physician can pull on the tether and retract the valve implant 10 as shown in FIG. 19B. If, on the other hand, it is determined that placement of the valve implant 10 has been successful, then the physician simply cuts the tether and pulls the free end out of from the proximal legs 44 and out of the delivery device as shown in FIG. 19A.

Operation

Referring now to FIGS. 10-19, the operation of the present invention is explained. Each of the following figures will include two drawings, a drawing that shows the position of the handle 58, and a drawing of the corresponding catheter configuration.

Referring now to FIG. 10, the first step a physician takes in using the delivery device 50 to place a valve implant 10 in a leaflet of a native valve is to use a guidewire 60 to locate the site of the native valve. The guidewire 60 is thus threaded through the necessary blood vessels to the site of the native valve. For example, if it were desired to place the valve implant 10 in, or between, the leaflets of the aortic valve, the guidewire 60 would be placed percutaneously in the femoral artery, or other suitable arterial access, advanced up the aorta, around the arch, and placed above the target leaflet of the aortic valve. Once the guidewire 60 is in place, the catheter delivery system 50 is advanced along the guidewire 60.

Figures 10A, 10B:
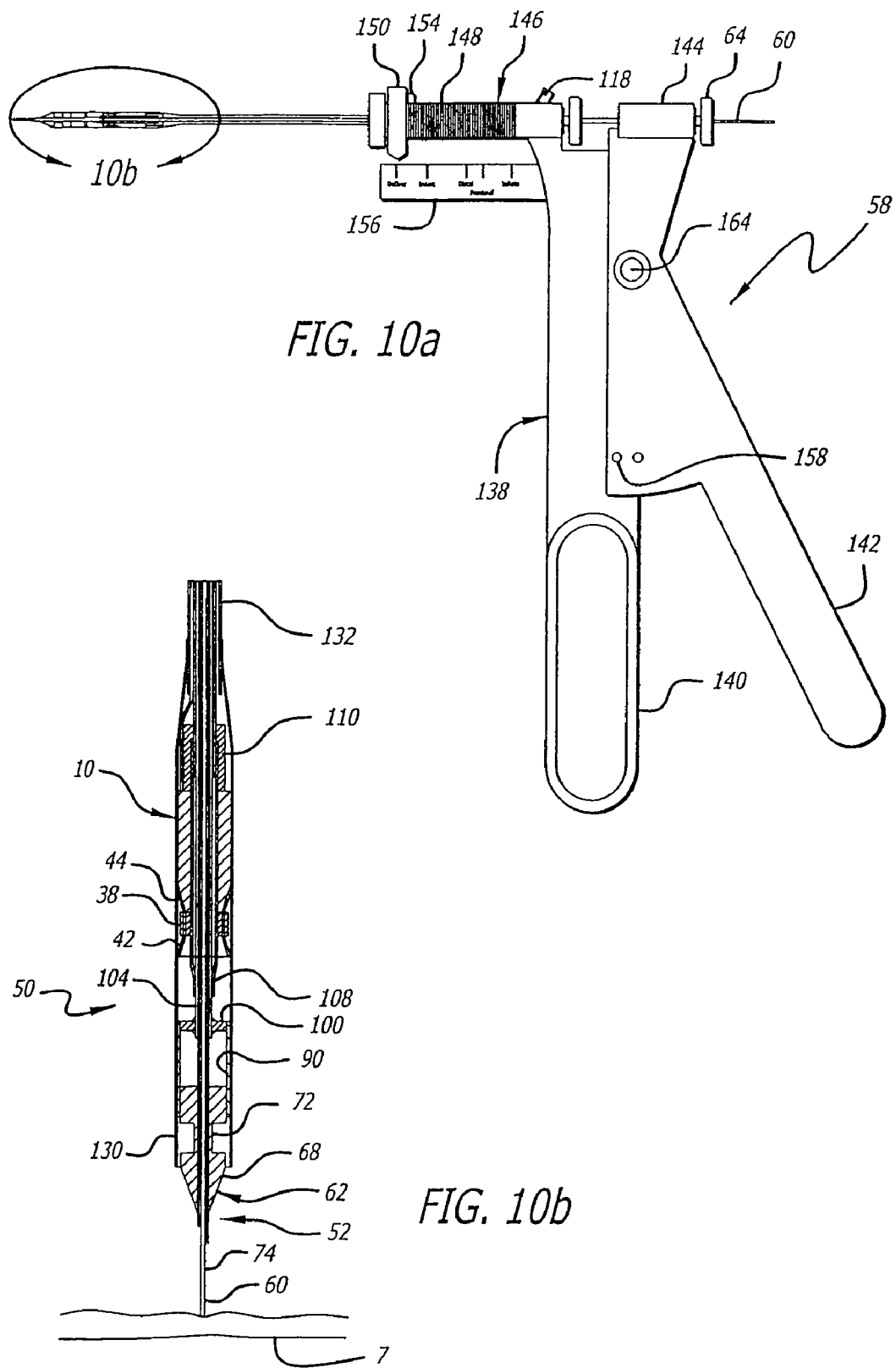

In FIG. 10*a*, it can be seen that the target leaflet 7 has been located with the guidewire 60 and the catheter delivery system 50 has been advanced along the guidewire 60 the target leaflet 7. Positioning the catheter delivery system 50 on the target leaflet 7 may be aided using imaging methods such as fluoroscopy and/or ultrasound. FIG. 10*a* shows that when this step is performed, the sheath retraction nut 150 is in the "Deliver" position as shown on the sheath retraction indicator 156. In the "Deliver" position, the sheath 130 covers the capture groove 72 of the cutter die 62. The cutter 90 remains retracted proximal of the capture groove 72. Also, the conical distal end 68 of the cutter die 62 extends from the distal end of the sheath 130.

In this regard, it is helpful to note that the target leaflet may actually include two leaflets if the leaflets are calcified together. For example, with reference to FIG. 1, if two leaflets have become calcified together along their edges or lines of coaptation, the present invention contemplates cutting a hole in a manner that traverses the leaflet edges and thereafter inserting a valve (as explained below) across both leaflet edges.

Once satisfied that the target site has been reached with the catheter delivery system 50, the next step is to traverse the tissue of the target valve leaflet 7. However, before the cutter die 62 is advanced through the leaflet tissue 7, the sheath catheter 56 must be retracted until the "Insert/Cut" position has been achieved. This is accomplished by rotating the threaded sheath retraction nut 150 until the nut 150 is aligned with the "Insert/Cut" marking on the sheath retraction indicator 156. Rotating the sheath retraction nut 150 causes the nut 150 to act against the tab 154 of the sheath hub 134.

Figure 11A:
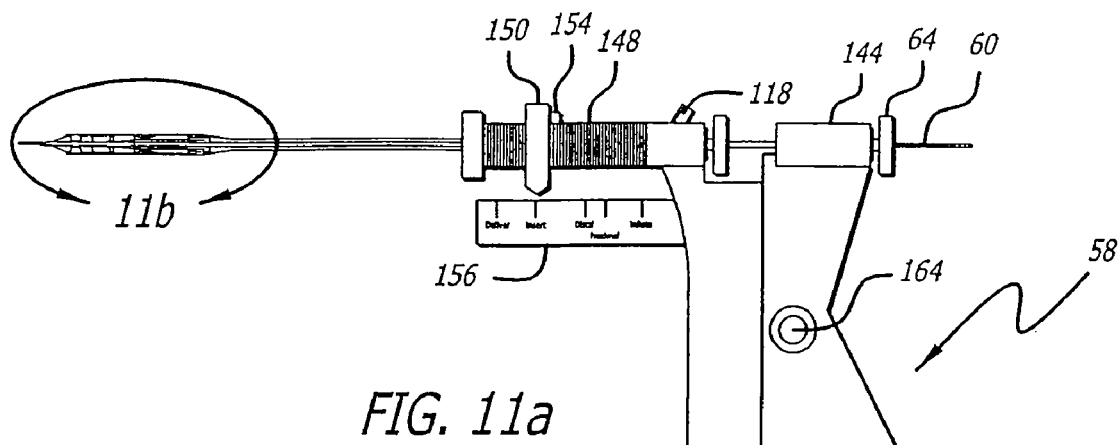
FIG. 11a is a side elevation of the handle of the present invention in an "Insert" position.
Figure 11B:
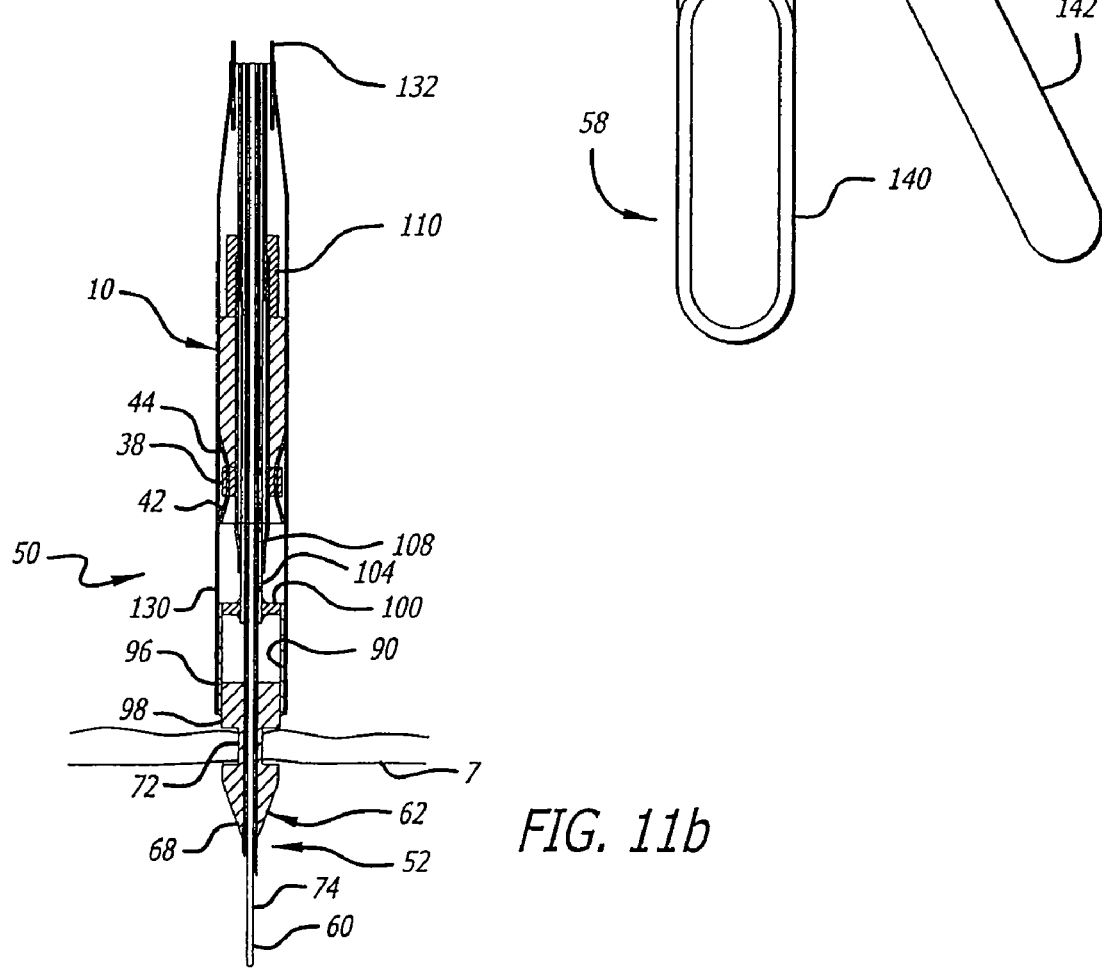

Referring now to FIGS. 11*a* and 11*b*, it can been seen that the target valve leaflet 7 has been punctured by either the guidewire 60, in the event that a sufficiently sharp guidewire is being used, or more preferably, the needle tip 74 of the leaflet capture catheter 52. When the needle tip 74 of the leaflet capture catheter 52 is used to puncture the leaflet, the guidewire 60 is first retracted so that it does not extend through the needle tip 74.

In one embodiment, the needle may be configured to have a hollow sharp shaft followed by a conical shank (not shown). This will allow the needle to create an initial penetration of the tissue followed by a more traditional puncturing action from the conical shank A needle configured in this manner will also assist in positioning the delivery device over each leaflet.

The cutter die 62 is advanced through the leaflet 7 until the leaflet 7 snaps into the capture groove 72. The conical distal end 68, as it is being advanced through the leaflet 7, will provide an increasing resistance that is tactily perceptible to the physician. Once the leaflet 7 encounters the flat portion 70, the physician will detect a decreased resistance and can expect a snap when the resilient tissue snaps into the capture groove 72. The guidewire 60 is then re-advanced into the ventricle (assuming the aortic valve is the target valve).

In this regard, it is notable that in one embodiment of the invention, the guidewire could be fabricated to include a transducer at its distal end (not shown). The guidewire could then be used to measure ventricular pressure (e.g., left ventricular pressure when treating the aortic valve) and thus provide the physician greater ability to monitor the patient during the procedure.

Once the physician is convinced that the leaflet 7 has entered the capture groove 72, the cutting step may commence. Referring now to FIGS. 12a and 12b, the cutting step is demonstrated. Cutting is performed by depressing safety button 158 and squeezing the actuator 142. After the safety button 158 and the actuator 142 are squeezed, the spring loaded safety button on 158 will travel from a first hole 160 in the actuator 142 to a second hole 162. When the safety button 158 reaches the second hole 162, it will snap into the second hole 162, thereby locking the actuator 142 in place. This ensures that the cutter die is retracted into the cutter 90, but that excess pressure is not placed on either the cutter die 62 or the cutter 90. When the actuator 142 is squeezed, cutting is effected because the actuator 142 rotates, relative to the handle body 138, around the pivot pin 164. This action causes the leaflet capture catheter bracket 144 to move in a proximal direction thereby pulling the hemostatic hub 64 with it. Pulling the hub 64 causes the cannula 66 and the cutter die 62 attached thereto, to be pulled in a proximal direction relative to the delivery catheter 64. The cutter die 62 enters the cutter 90, thereby cutting the tissue. The clearance between the cutter die 62 and the cutter drum 96 is sufficiently minimal to prevent the occurrence of hanging "chads" in the cut. Additionally, the sharpened cutting tip 98 of the cutter 90 may be cut at an angle, or even include a point, such that the entire cut does not have to be initiated around the entire circumference of the cutter drum 96 simultaneously.

Figure 13A:
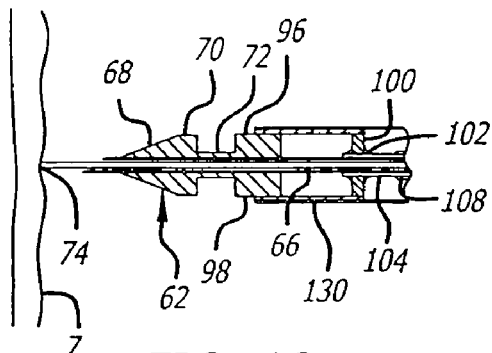
FIGS. 13a-e are an operational sequence of the capture device of FIG. 6 interacting with the cutting drum of FIG. 7a to remove and capture a section of tissue from a target valve leaflet.
Figure 13B:
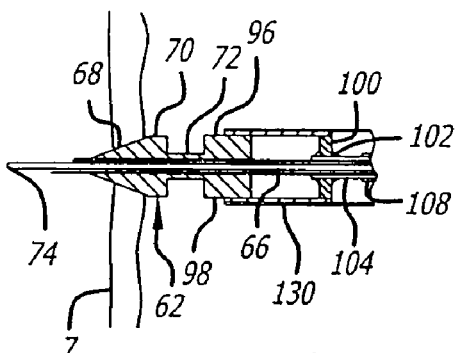
Figure 13C:
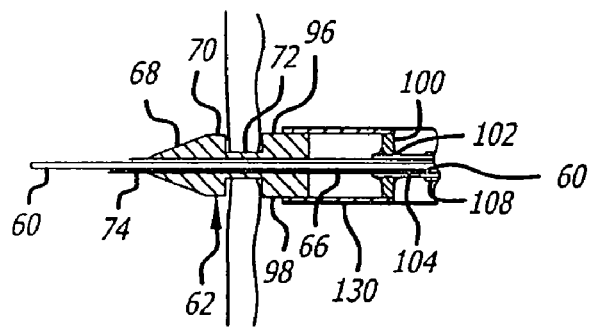
Figure 13D:
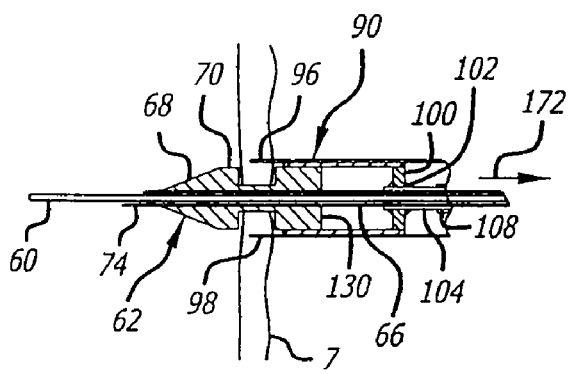

A more detailed view of the cutting action of the cutter die 62 and the cutter 90 is shown in FIGS. 13a-13e. In FIG. 13a, the needle tip 74 of the cannula 66 has just reached the leaflet 7. The sheath 130 has been retracted to the "Insert/Cut" position as indicated by the exposed capture groove 72 of the cutter die 62. In FIG. 13b, the cutter die 62 is being advanced through the target leaflet 7 such that the target leaflet 7 has reached the conical distal end 68 of the cutter die 62. In FIG. 13c, the conical distal end 68 and the flat portion 70 of the cutter die 62 have passed completely through the target leaflet 7, and the target leaflet 7 has snapped into the capture groove 72. Additionally, the guidewire 60 has been re-advanced through the leaflet capture catheter 52 so that it extends beyond the needle tip 74. The guidewire 60 will be used to retain the position of the hole cut through the leaflet 7 after the cutter die 62 is retracted. In FIG. 13d, the physician has begun to cut by squeezing the actuator 142 (FIG. 12a), as evidenced by the advancement of the cutter 90. The cutting tip 98 of the cutter 90 has been advanced mid-way through the target leaflet 7. This movement is relative to the position of the cutter die 62. More accurately, the cutter die 62 is being retracted into the cutter 90, bringing with it the tissue of the leaflet 7. The movement of the cutter die 62 is evidenced by arrow 172.

Figure 13E:
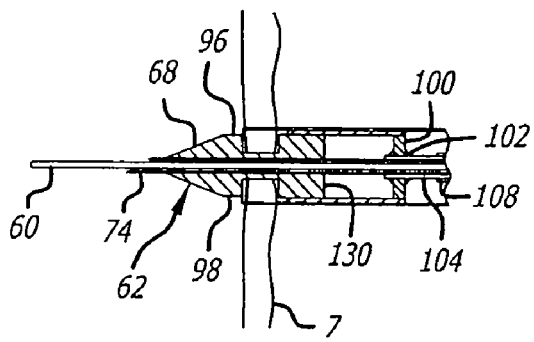

In FIG. 13e, the cut is complete as the actuator 142 has been squeezed enough so that the safety button 158 has found the second hole 162 (FIG. 12a), as evidenced by the position of the cutter die 62. The cutter die 62 is retracted enough such that the capture groove 72 is completely housed within the cutter drum 96. Notably, the cut tissue of the leaflet 7 remains trapped between the capture groove 72 and the cutter drum 96. The trapping of this tissue prevents the tissue from traveling downstream through the blood vessel and causing damage.

Figure 14A:
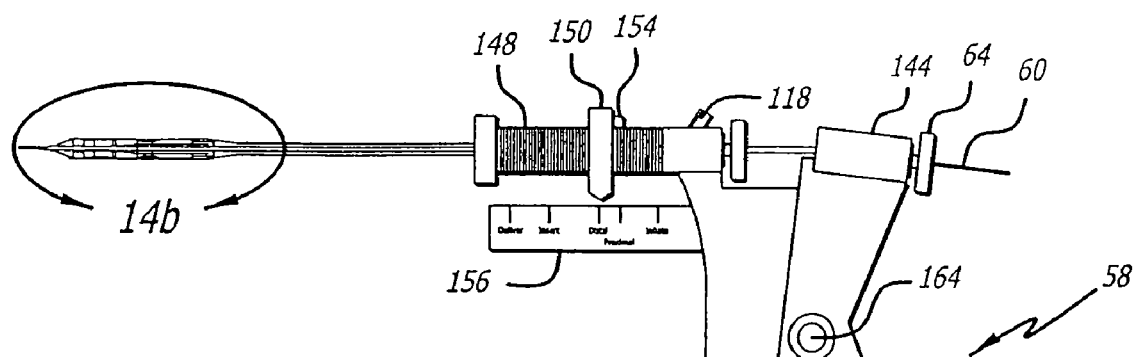
FIG. 14a is a side elevation of the handle of the present invention in a "Distal" position.
Figure 14B:
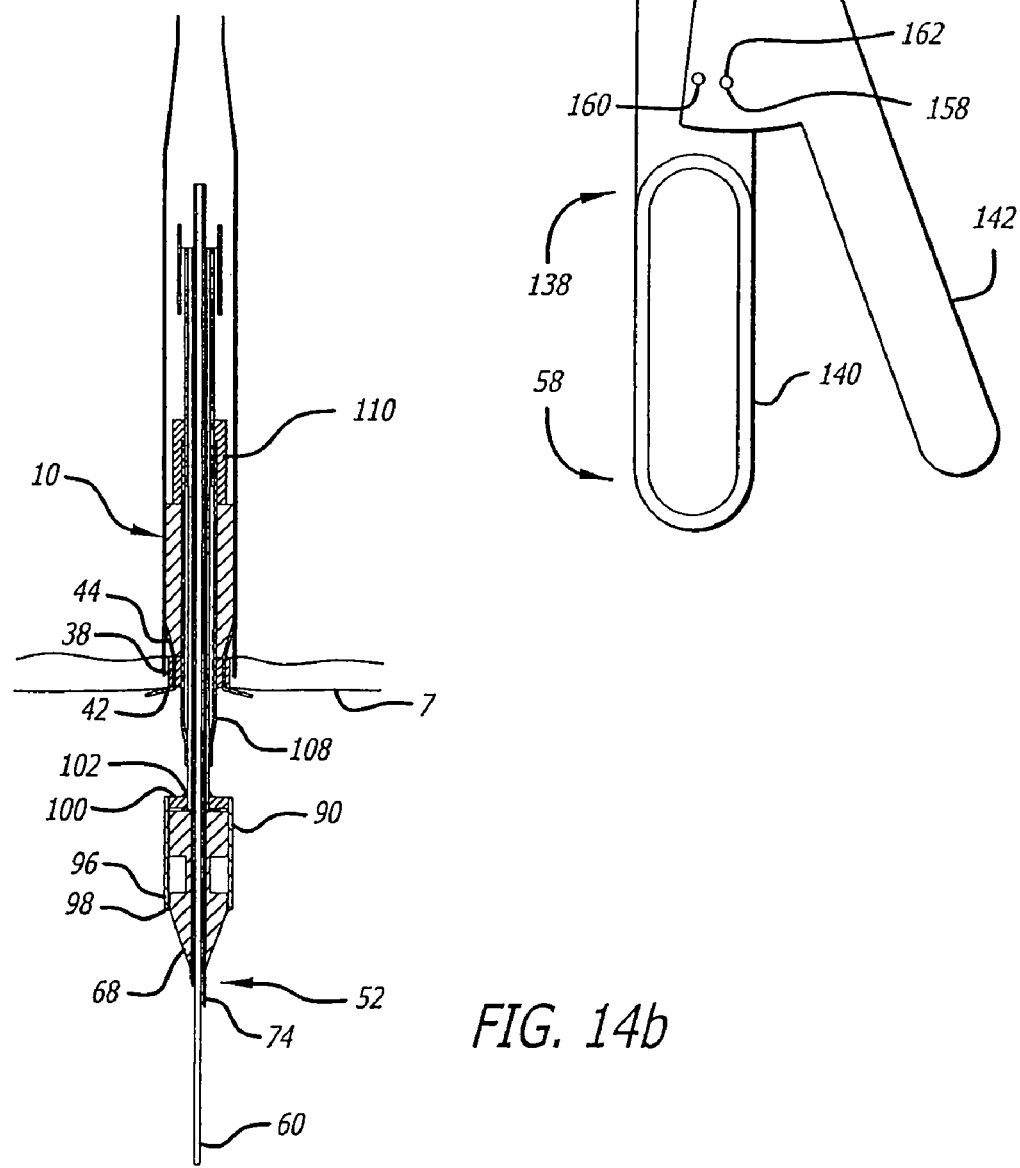

Referring now to FIGS. 14a and 14b, once the hole in the tissue 7 is cut, the step of placing the valve implant 10 begins. First, the entire delivery system 50 is moved distally deeper into the patient such that the distal legs 42 pass through the newly formed hole in the tissue 7. It is important that at least the distal legs 42 are located on the upstream (ventricle) side of the tissue 7 prior to deploying the valve implant 10. Once the physician is confident that the distal legs 42 extend beyond the valve leaflet tissue 7, the sheath 130 may be retracted to release the distal legs 42. This is accomplished by rotating the sheath retraction nut 150 until the sheath retraction nut 150 aligns with the "Distal" marking on the sheath retraction indicator 156. Doing so causes the sheath retraction nut 150 to act against the tab 154 thereby withdrawing the sheath 130 until just the distal legs 42 are exposed. The distal legs 42 are preloaded such that they spring outwardly, as shown in FIG. 14b, when uncovered by the catheter sheath 130. The distal legs 42 are long enough to extend beyond the radius of the sheath 130, such that they may act against the valve leaflet tissue 7. Once the sheath retraction nut 150 has been rotated to the "Distal" position on the indicator 156, the physician may pull the catheter delivery system 50 in a proximal direction until he or she feels the distal legs 42 catch or act against the valve leaflet tissue 7. Notably, the actuator 142 remains locked in the position it was placed in during the cutting procedure. Leaving the actuator 142 in this position ensures that the valve leaflet tissue trapped between the cutter die 62 and the cutter drum 96 is not released.

Figure 15A:
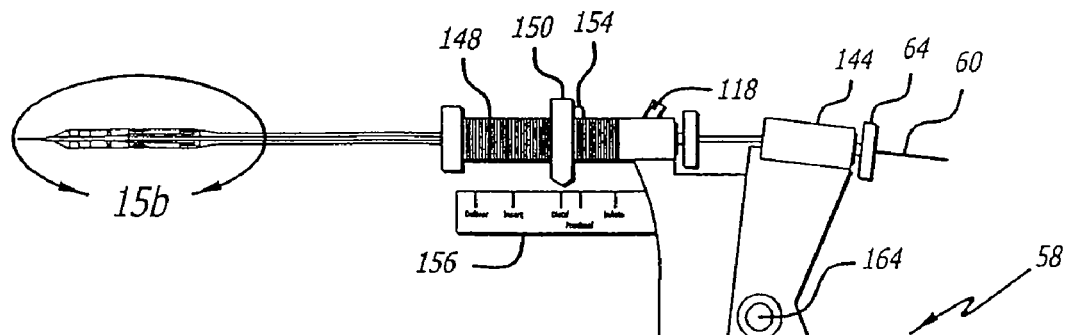
FIG. 15a is a side elevation of the handle of the present invention in a "Proximal" position.
Figure 15B:
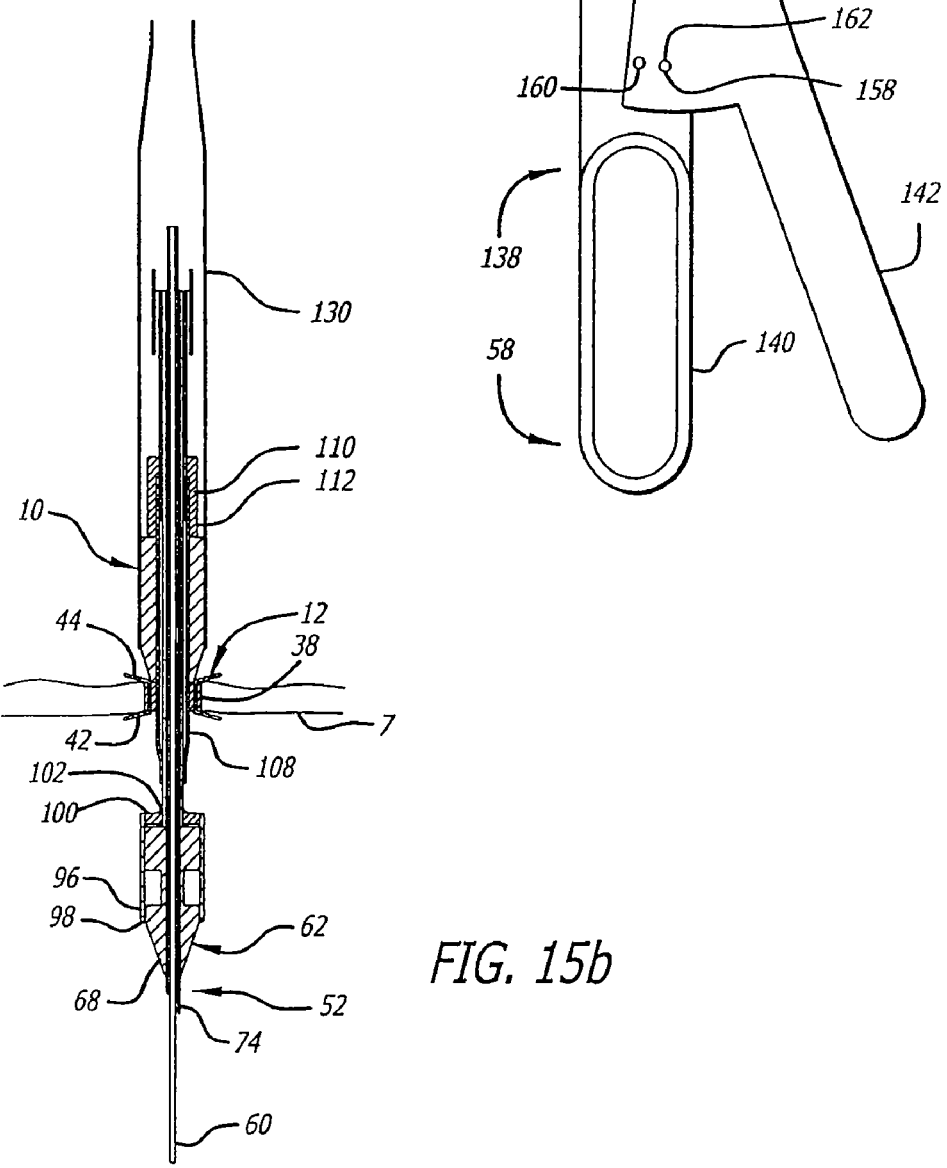

The next step is illustrated in FIGS. 15a and 15b. The physician maintains the contact between the distal legs 42 and the valve leaflet tissue 7. While maintaining this contact, the sheath retraction nut 150 is rotated to the "Proximal" position as indicated on the marker of the sheath retraction indicator 156. Rotating the sheath retraction nut 150 again acts against the tab 154 causing the sheath 130 to retract further. When the proximal position has been achieved, the sheath will be retracted enough to release the proximal legs 44. Like the distal legs 42, the proximal legs 44 will spring outwardly when released by the sheath 130. The proximal legs 44 act against the opposite side (aorta side) of the valve leaflet tissue 7 sandwiching the valve leaflet tissue 7 between the distal legs 42 and the proximal legs 44. The valve implant 10 is now attached to the patient.

Figure 16A:
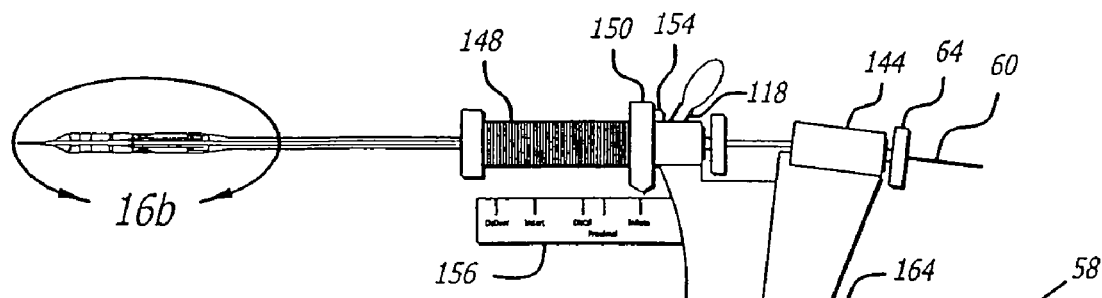
FIG. 16a is a side elevation of the handle of the present invention in an "Inflate" position.
Figure 16B:
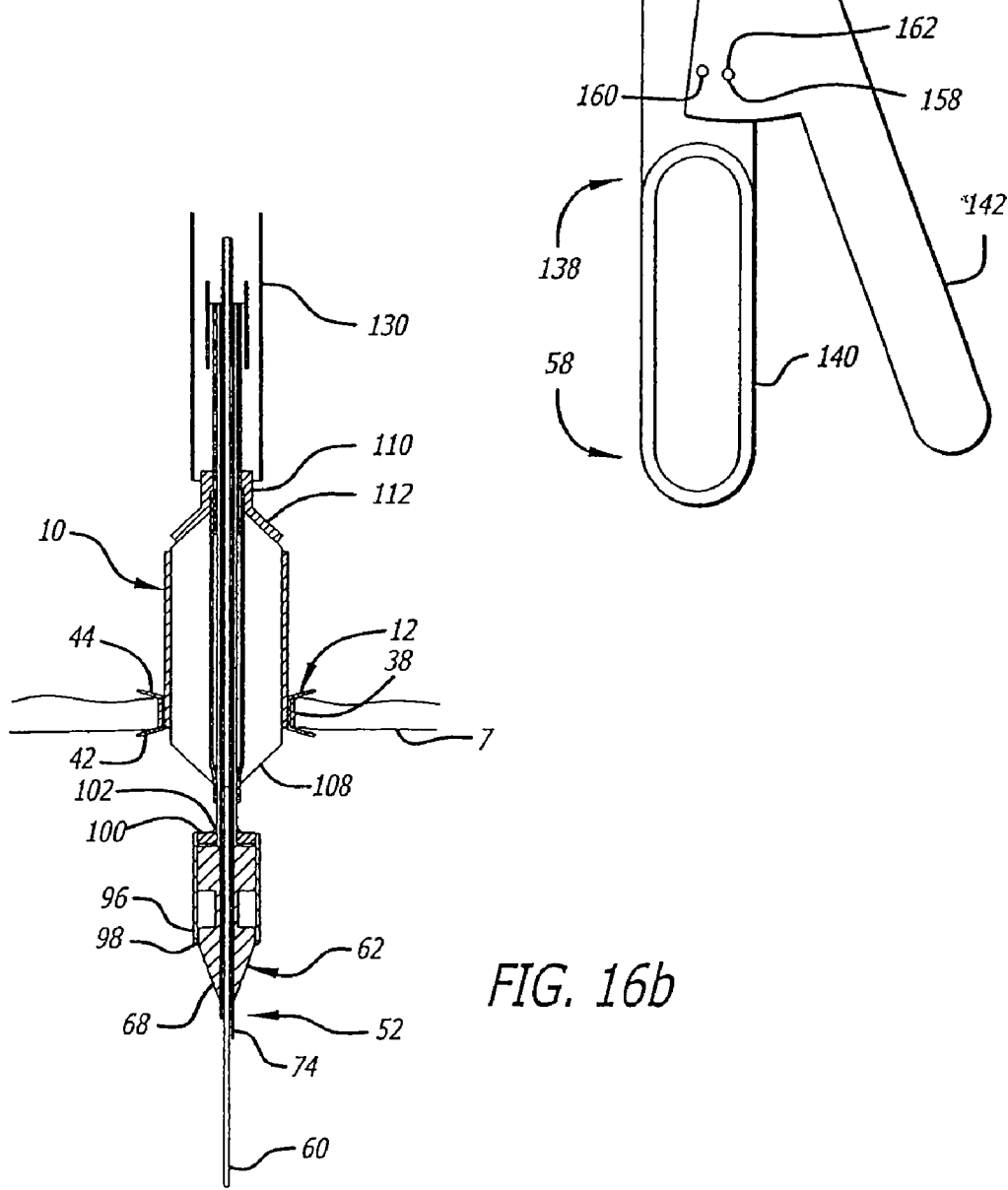
FIG. 16b is a sectional view of the distal end of the delivery system of the present invention when the handle is in the "Inflate" position of FIG. 16a and a balloon of the delivery system is inflated.

The next step is to inflate the balloon 108 thereby expanding the valve implant 10. This step is best shown in FIGS. 16a and 16b. The physician further rotates the sheath retraction nut 150 to the "Inflate" position on the indicator 156. The sheath retraction nut 150 again acts against the tab 154 thereby retracting the sheath 130 to a point where the valve stop 110 is at least partially exposed and the flexible sleeve 112 of the valve stop 110 is completely exposed.

Once the sheath 130 has been retracted to the "Inflate" position on the indicator 156, the balloon 108 may be inflated. This is accomplished by injecting fluid into the balloon inflation port 118. Fluid is injected until the sizing ring 38 has achieved its maximum diameter. The physician will feel resistance against further inflation by the sizing ring 38. Additionally, the sizing ring 38 or other parts of the anchoring mechanism 12 may be constructed of a radiopaque material such that monitoring can be accomplished using X-ray equipment. The use of the sizing ring 38 is not required for the practice of the invention. It is, however, preferred in the preferred embodiments of the invention.

Figures 17A, 17B:
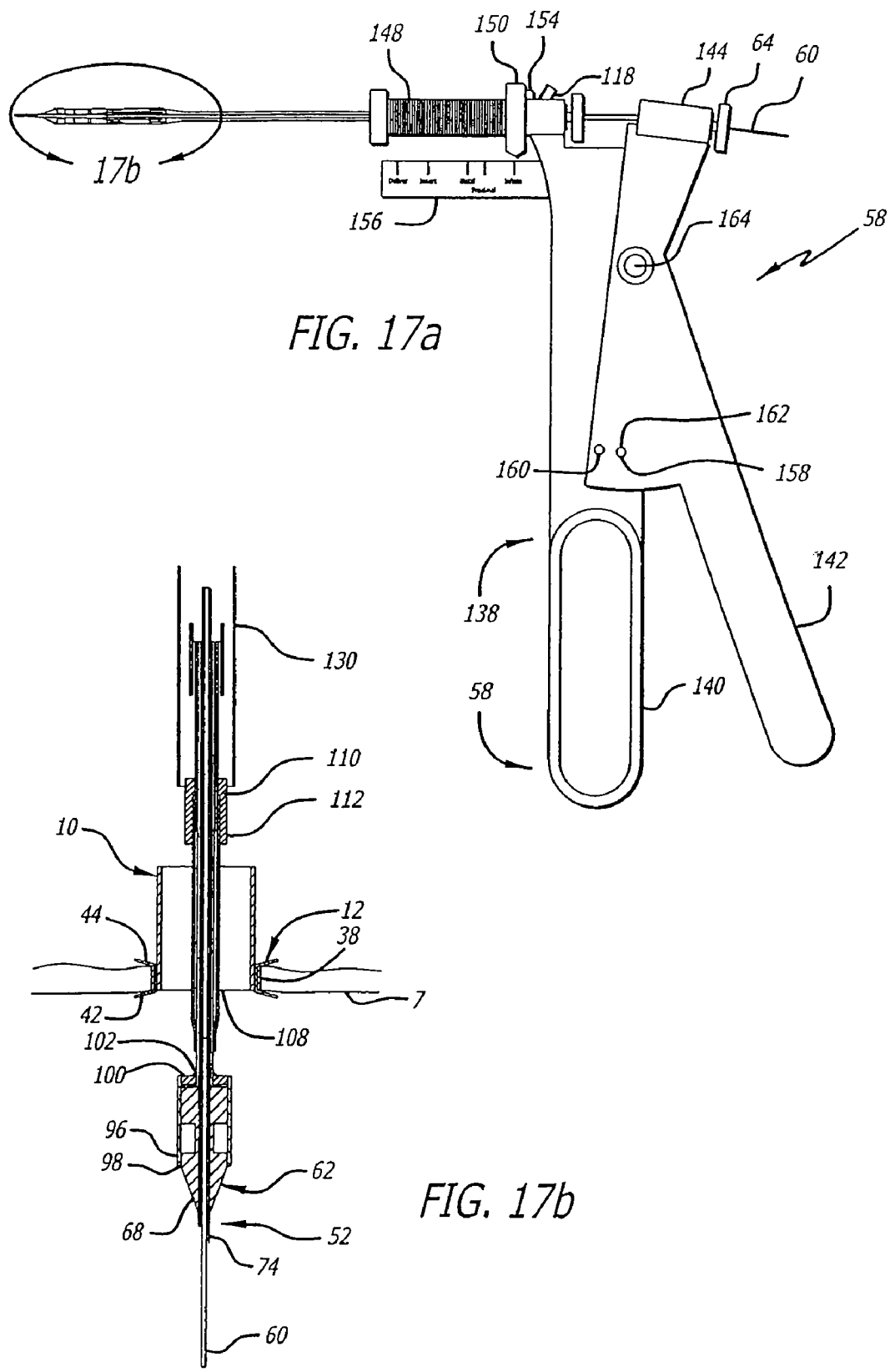
FIG. 17a is a side elevation of the handle of the present invention in an "Inflate" position during a deflating procedure.
FIG. 17b is a sectional view of the distal end of the delivery system of the present invention when the handle is in the "Inflate" position of FIG. 17a and the balloon of the delivery system has been deflated.
Figure 18:
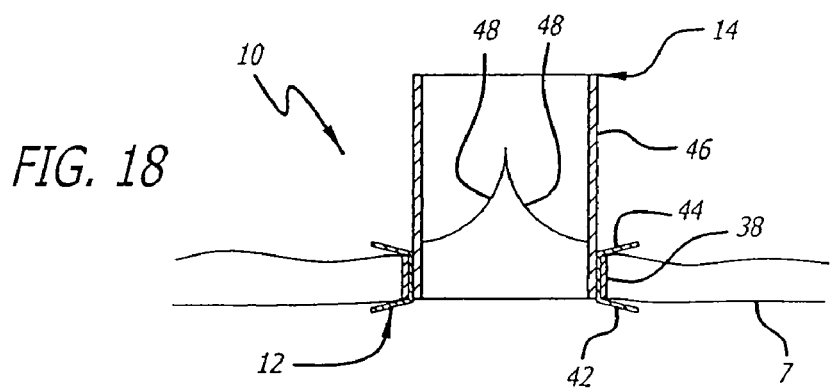
FIG. 18 is a sectional view of a valve implant of the present invention in a deployed configuration.

Once the inflation of the balloon 108 is complete, the next step involves deflating the balloon 108. This is illustrated in FIGS. 17a and 17b. Deflating the balloon involves simply withdrawing fluid through the balloon inflation port 118. As is shown in FIG. 17b, when the balloon 108 is deflated, the valve implant 10 retains its inflated proportions. These inflated proportions allow easy retraction of the catheter delivery system through the valve implant 10. As is best seen in FIG. 18, once the delivery system 50 has been retracted, the valve implant 10 remains attached to the valve leaflet tissue 7.

Figure 21:
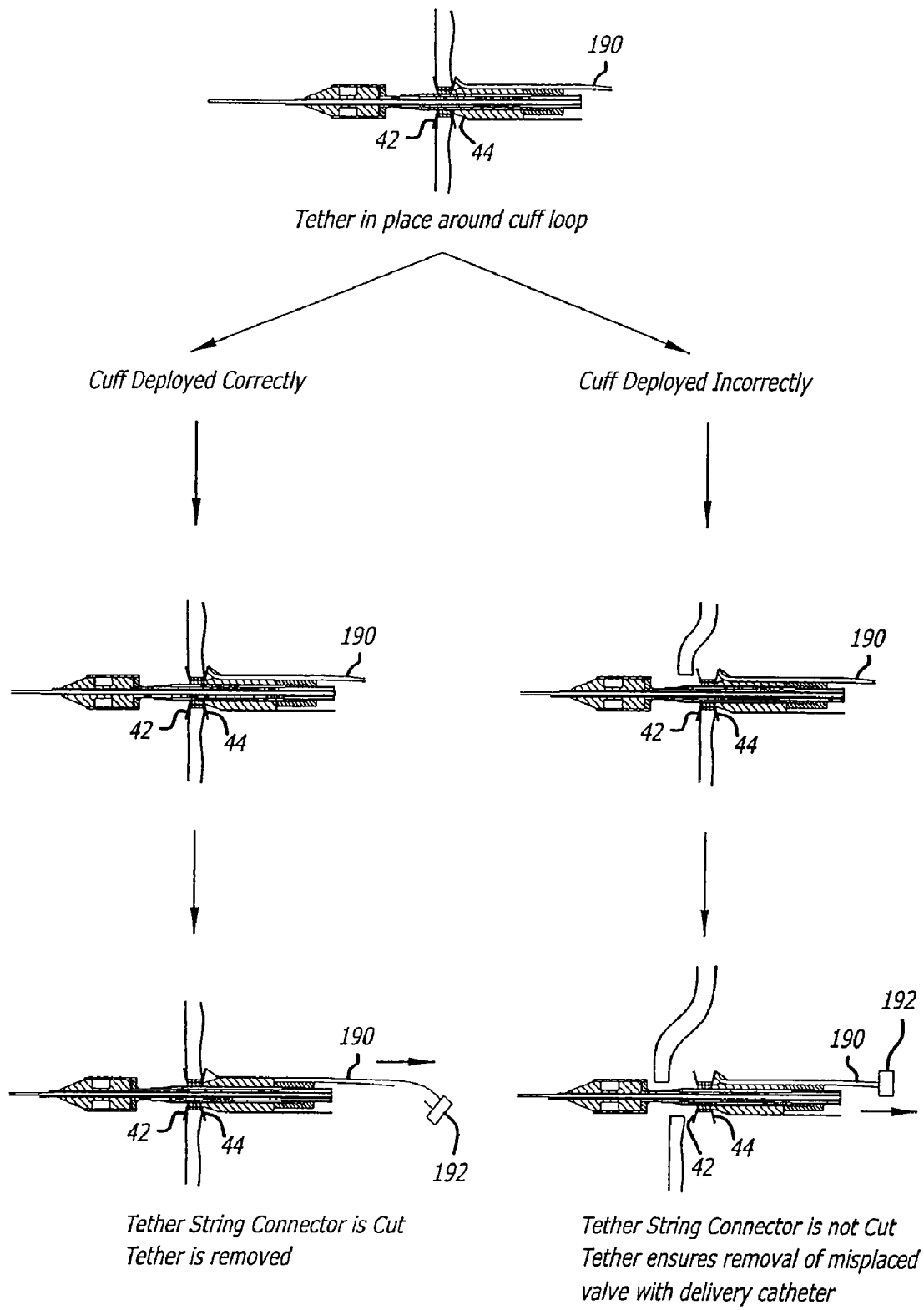
FIG. 21 is a flow chart figure showing a tether retraction system for use in a catheter delivery system in accordance with the present invention.
Figure 22A:
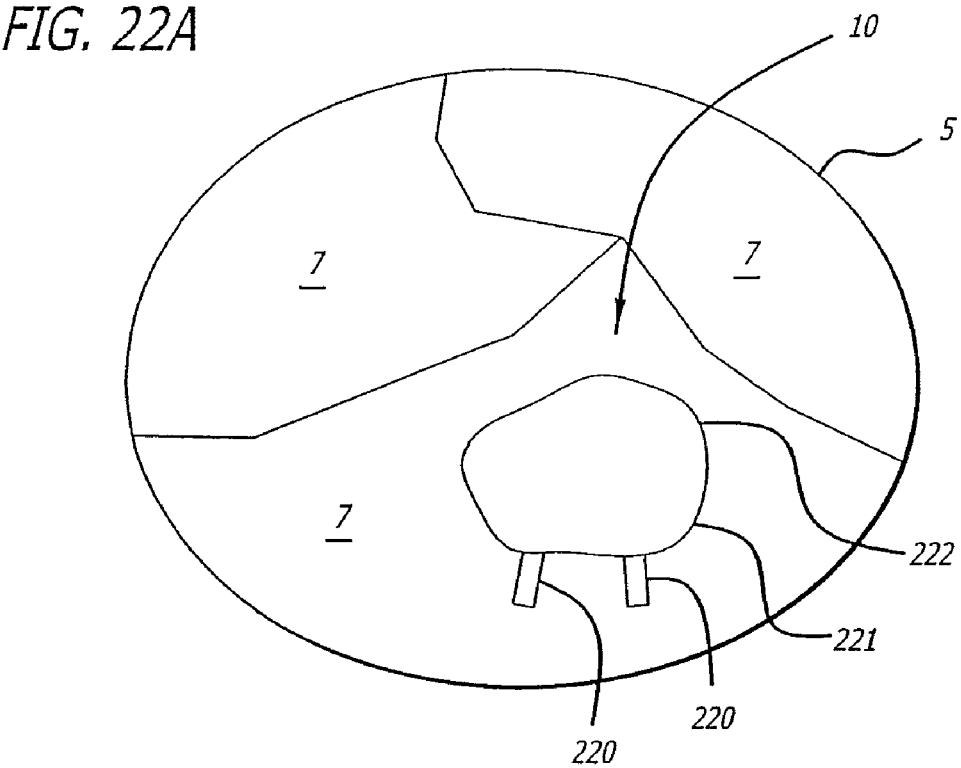
FIGS. 22A and 22B are top views of a hinged valve in accordance with another preferred embodiment of the present invention.
Figure 22B:
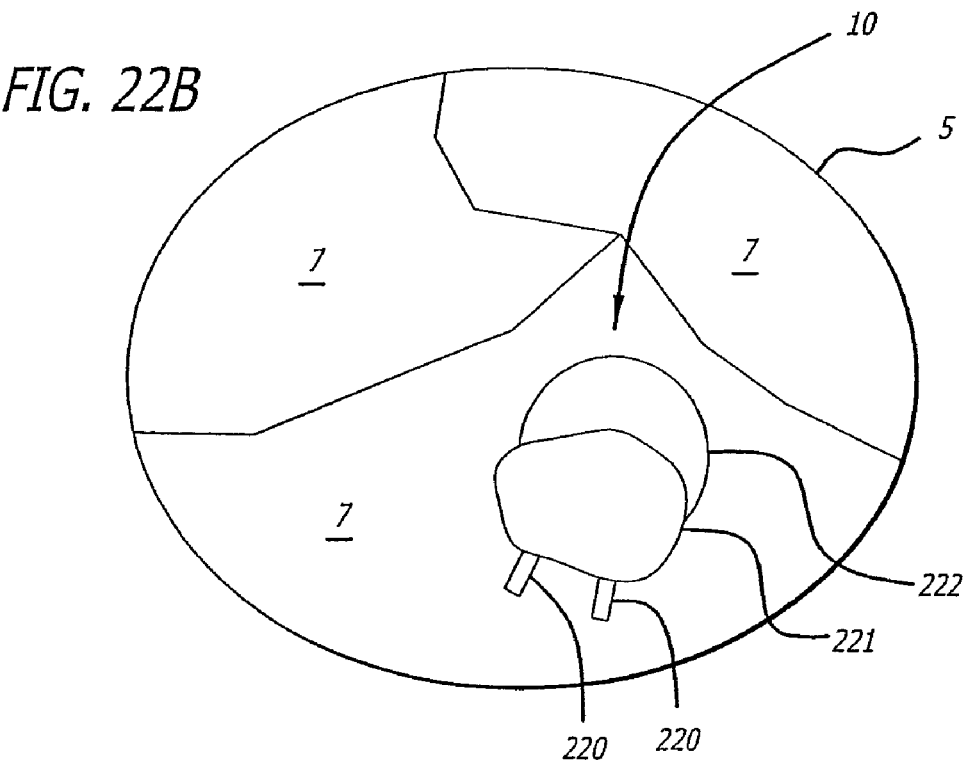
Figure 23A:
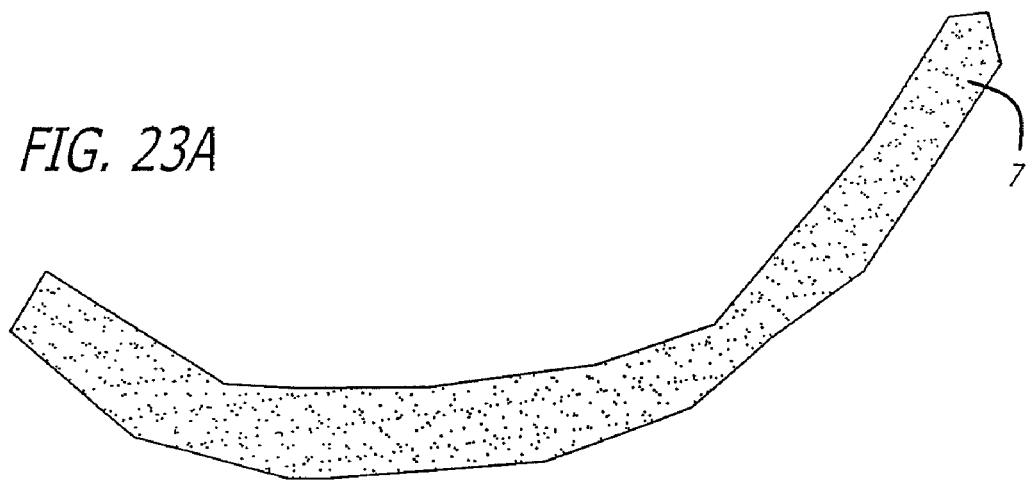
FIGS. 23A, 23B and 23C are cross-sectional views of a hinged valve in accordance with the present invention; and, FIGS. 24A and 24B are cross-sectional views of a hinged valve in accordance with the present invention.
Figure 23B:
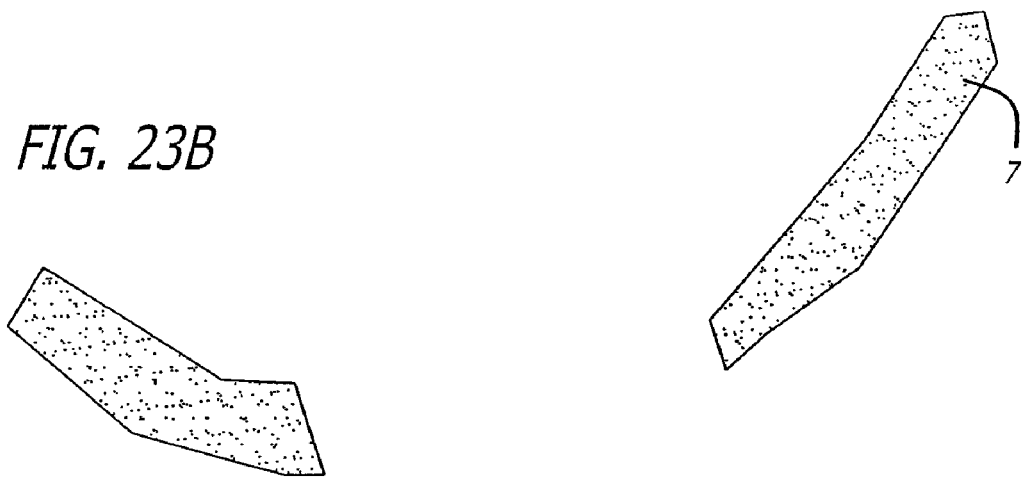
Figure 23C:
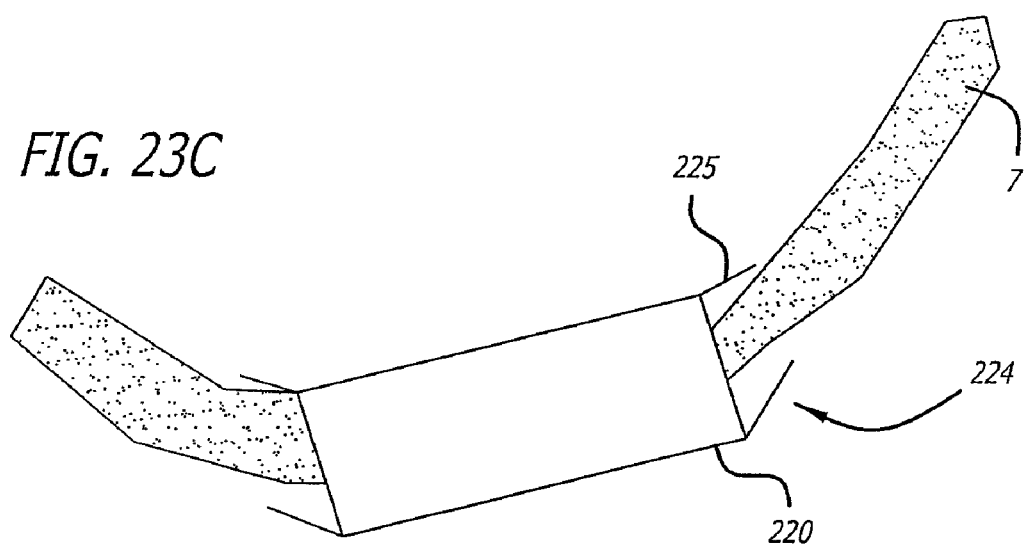

As discussed above with reference to FIGS. 19A, 19B and 20, one embodiment of the catheter delivery device 50 and the valve implant 10 includes the use of a tether 190 to allow the physician to retract the valve implant 10 in the event of improper deployment. With reference to FIG. 21, the operation of the tether 190 under both proper deployment and improper deployment is disclosed.

On the left side of FIG. 21, it is seen that the valve implant 10 has been properly deployed in the valve leaflet. As a result, the physician cuts the tether 190 and pulls the tether away from the catheter handle from the proximal legs 44 of the cuff.

On the right side of FIG. 22, it is seen that the valve implant 10 has been improperly deployed insofar as the legs of the cuff have not adequately grasped the edge of the hole in the leaflet. As a result, the physician may retract the valve implant 10 by pulling on the tether 190 and thus removing the valve implant 10 from its improperly deployed location

What is claimed is:

1. A heart valve, transluminally deliverable via a catheter, comprising:
    a mesh housing; and,
    a flow control mechanism of biologic tissue coupled to said housing, said flow control mechanism including passive leaflets, free from biasing mechanisms;
    said housing including an anchoring mechanism having at least one end free to extend radially to affix the heart valve to tissue of a leaflet of a native heart valve;
    wherein said mesh housing is adapted to be compressed into the catheter for transluminal delivery, and to expand to a desired diameter upon deployment from said catheter.

2. A heart valve according to claim 1, wherein said at least one end comprises an expandable cuff for engaging a leaflet of a native human heart valve.

3. A heart valve according to claim 2, wherein said cuff includes a plurality of radial extensions extending from said cuff and engageable with said leaflet of a native heart valve so as to secure said cuff in said leaflet of a native heart valve.

4. A heart valve according to claim 1, wherein said flow control mechanism comprises a sleeve containing a plurality of valve members.

5. A heart valve according to claim 4, wherein said plurality of valve members includes leaflets disposed on a stent form.

6. The heart valve of claim 1, wherein said mesh housing is comprised of Nitinol.

7. The heart valve of claim 1, wherein said anchoring mechanism includes an upstream and downstream component for further fixating said housing.

8. The heart valve of claim 7, wherein said upstream and downstream components fold outwardly when released.

9. A device, transluminally deliverable via a catheter, to increase fluid flow through a mammalian valve comprising:
    a valve mechanism, of biologic tissue, containing a lumen therein;
    said valve mechanism actuatable so as to place said lumen in one of an open and closed state;
    said valve mechanism including leaflets that are passive, influenced to one of said open and closed states only by fluid flow; and,
    a housing connected to said valve mechanism;
    said housing including an anchoring structure with an end free to extend radially against tissue of a leaflet of said mammalian valve;
    wherein said housing is constructed of mesh, allowing the housing to be compressed into a catheter for delivery and expands to a desired diameter upon deployment from said catheter.

10. The heart valve of claim 9, wherein said housing is comprised of Nitinol.

11. The heart valve of claim 9, wherein said anchoring structure includes an upstream and downstream component for further fixating said housing structure.

12. The heart valve of claim 11, wherein said upstream and downstream components fold outwardly when released.

13. A valve device, transluminally deliverable via a catheter, for treating a diseased valve comprising:
    a fluid flow control element comprised of biologic tissue, said fluid flow control element including passive leaflets, free from biasing mechanisms;
    a housing structure constructed of a stiff fabric and having an outwardly radiating free end for anchoring said fluid flow control element adjacent to tissue of a native valve leaflet;
    said fluid flow control element and said stiff fabric structure being connected to each other.

14. The heart valve of claim 13, wherein said mesh housing structure is comprised of Nitinol.

15. A valve device according to claim 13, wherein said housing structure includes a cuff.

16. A valve device according to claim 13, wherein said housing structure is expandable and includes a constraining device for constraining the expansion of said stiff fabric structure.

17. A heart valve, transluminally deliverable via a catheter, comprising: a compressible and expandable housing with a free end extending radially from at least one of two opposite ends of said stiff fabric body; and a prosthetic valve comprised of biologic material attached to an inside surface of said housing, said prosthetic valve including passive leaflets, free from biasing mechanisms, said housing constructed of a stiff fabric.

18. A heart valve, transluminally deliverable via a catheter, comprising:
    a housing structure;
    a flow control mechanism coupled to said position securement structure, said flow control mechanism including passive leaflets, free from biasing mechanisms;
    said mesh housing having a position securement structure including an end that is free to radiate outwardly to engage a surface of a leaflet of a native heart valve;
    wherein said housing structure comprises a mesh tube, allowing said entire housing structure to be expandable and collapsible.

* * * * *